United States Patent [19]

della Valle et al.

[11] Patent Number: 4,957,744

[45] Date of Patent: * Sep. 18, 1990

[54] CROSS-LINKED ESTERS OF HYALURONIC ACID

[75] Inventors: Francesco della Valle, Padova; Aurelio Romeo, Rome, both of Italy

[73] Assignee: Fidia, S.p.A., Abano Terme, Italy

[*] Notice: The portion of the term of this patent subsequent to Jul. 25, 2006 has been disclaimed.

[21] Appl. No.: 106,658

[22] Filed: Oct. 13, 1987

[30] Foreign Application Priority Data

Oct. 13, 1986 [IT] Italy ............................. 48546-A/86

[51] Int. Cl.$^5$ .................... A61K 31/70; C07G 3/00; C07H 1/00
[52] U.S. Cl. .................................. 424/401; 424/423; 424/443; 424/451; 424/489; 512/5; 514/54; 514/844; 514/880; 536/55.1
[58] Field of Search ................ 536/55.1; 514/54; 424/423, 443, 489, 401

[56] References Cited

U.S. PATENT DOCUMENTS

| | | | |
|---|---|---|---|
| 4,060,081 | 11/1977 | Yannas et al. | 128/156 |
| 4,141,973 | 2/1979 | Balazs | 514/54 |
| 4,280,954 | 7/1981 | Yannas et al. | 260/123.7 |
| 4,322,523 | 3/1982 | Wagner | 536/1.1 |
| 4,328,803 | 5/1982 | Pape | 128/276 |
| 4,440,926 | 4/1984 | Mardiguian | 536/21 |
| 4,487,865 | 12/1984 | Balazs et al. | 524/29 |
| 4,500,676 | 2/1985 | Balazs | 525/54.2 |
| 4,582,865 | 4/1986 | Balazs et al. | 524/29 |
| 4,605,691 | 8/1986 | Balazs et al. | 524/27 |
| 4,636,524 | 1/1987 | Balazs | 514/781 |
| 4,703,108 | 10/1987 | Silver et al. | 530/356 |
| 4,713,448 | 12/1987 | Balazs | 536/55.1 |
| 4,772,419 | 9/1988 | Malson et al. | 252/315.1 |
| 4,851,521 | 7/1989 | della Valle et al. | 536/55.1 |

FOREIGN PATENT DOCUMENTS

| | | |
|---|---|---|
| 0044228 | 1/1982 | European Pat. Off. . |
| 0161887 | 11/1985 | European Pat. Off. . |
| 0193510 | 9/1986 | European Pat. Off. . |
| 0216453 | 4/1987 | European Pat. Off. . |
| 0224987 | 6/1987 | European Pat. Off. . |
| 0280807 | 9/1988 | European Pat. Off. . |
| 0291177 | 11/1988 | European Pat. Off. . |
| 3434082 | 9/1984 | Fed. Rep. of Germany . |
| 2478468 | 9/1981 | France . |
| WO86/00079 | 1/1986 | PCT Int'l Appl. . |
| WO87/07898 | 12/1987 | PCT Int'l Appl. . |
| 2151244 | 7/1985 | United Kingdom . |
| 2160097 | 12/1985 | United Kingdom . |
| 2185397 | 7/1987 | United Kingdom . |

OTHER PUBLICATIONS

Chemical Abstracts 92658y (Vikha et al.).

*Primary Examiner*—John W. Rollins
*Assistant Examiner*—Elli Peselev
*Attorney, Agent, or Firm*—Birch, Stewart, Kolasch & Birch

[57] ABSTRACT

Cross-linked esters of hyaluronic acid are provided which result from the esterification of polyhydric alcohols with two or more carboxy groups of the hyaluronic acid polysaccharide. These cross-linked esters are useful in the field of biodegradable plastics for sanitary and surgical articles and in the pharmaceutical and cosmetic fields for the preparation of useful compositions and articles.

91 Claims, No Drawings

CROSS-LINKED ESTERS OF HYALURONIC ACID

BACKGROUND AND FIELD OF THE INVENTION

The invention concerns esters of polyhydric alcohols of hyaluronic acid resulting from the esterification of such alcohols with two or more carboxy groups of the hyaluronic acid polysaccharide, esters which, due to the presence of bridge bonds between the above carboxy functions of the same or different molecules of hyaluronic acid, may be described by the term "cross-linked". These cross-linked esters may be total or partial and, in the latter, further carboxy functions may be esterified with monohydric or polyhydric alcohols, without the formation of cross-links (ester groups which shall also hereinafter be termed "simple"). In both types of cross-linked partial esters, non-esterified carboxy functions may be free or salified with metals or organic bases.

The invention also concerns the use of new cross-linked hyaluronic esters in the field of biodegradable plastic materials for the preparation of sanitary and surgical articles, in the pharmaceutical and cosmetic fields and, therefore, includes the various articles made with the same in such fields.

The specific use of the new esters may be seen in relation to the degree of cross-link esterification, that is the number of cross-linked groups of carboxy functions esterified with the above polyhydric alcohols, the number of simple esterified groups, and, lastly, also the number of salified groups, this degree of esterification or salification being itself related to the solubility of the product and to its viscous-elastic properties. Thus, for example, the total cross-linked esters are virtually insoluble in aqueous liquids and are very suitable, due to their molecular structure, for use in the making of plastic materials and resins and as additives for these materials. Esters with an average or low degree of esterification and their salts with inorganic or organic bases are more or less soluble in aqueous conditions and are suitable for the preparation of gels which may have many uses, both in cosmetics and pharmacology and in the medical-sanitary field in general.

The application for European patent No. 0 161887 of 3.5.85, published on 21.11.85, contains a description of some cross-linked derivatives of hyaluronic acid obtained by the reaction of epoxy compounds indicated as "polyfunctional". In the above patent publication, the term "polyfunctional epoxy compounds" means hydrocarbons with at least one epoxy function and possibly having also convertible functions in epoxy functions, the cross-linking reaction occurring through the epoxy groups. Of these functions, only the halogens are mentioned in the patent. Of these polyfunctional epoxy compounds only a few examples are mentioned in the above patent application, namely: epichlorohydrin, epibromohydrin, methylepichlorohydrin, methylepibromohydrin, 1,2-bis (2,3-epoxypropoxy)-ethane, 1,4-bis (2,3-epoxypropoxy)-butane, 1,6-bis (2,3-epoxypropoxy)-butane, 1,6-bis (2,3-epoxypropoxy)-hexane and a glycidyl ether of bisphenol A and bisphenol F. The preparation method used in this patent application, which is limited in the claims to the use of a halomethyloxyrane or a bisepoxy-compound, as well as being limited in its possible applications, gives cross-linked esters of hyaluronic acid with a low degree of esterification: in fact, as can be seen from the illustrative Examples of the patent application, a maximum of 4% esterification is reached in the case of reaction with epichlorohydrin (Example 4) to obtain a product with a low degree of solubility.

The present invention makes available a wide assortment of cross-linked esters, including particular esters wherein the ester groups, comprise radicals which are unsubstituted by a hydroxyl (as in the case of products resulting from the reaction of the above epoxides on hyaluronic acid or its salts). Importantly the invention provides mixed esters comprising a mixture of ester groups which are cross-linked and some ester groups which are not cross-linked, wherein the percentage of crosslinking groups may exceed 10% of all of the disaccharide units of hyaluronic acid.

The applications for UK patent No. 2 151 244 A of 13.8.1984, published on 17.7.1985, and the application for German Offenlegungsschrift No. 34 34 082 A1 of 17.9.1984, published on 11.7.1985, contain descriptions of some cross-linked derivatives of hyaluronic acid obtainable by the action on the same of formaldehyde, dimethylolurea, dimethylolethylenurea, a polyaziridine, a polyisocyanate and a divinylsulfone. Such derivatives are insoluble and are proposed, due to their biocompatibility, for in vivo applications in the form of various prosthetic articles, such as cardiac valves, vascular clips, etc., or may be added to the various polymeric materials used to make such articles. The same patents provide for the use of ethyl oxide as an agent to achieve "cross-linking", but the procedure is not illustrated, and neither is the type of product obtained. The structure of other cross-linked derivatives is not specified and no mention is made of the type of bonds forming the cross-linking. In the case of formaldehyde and of the above substituted ureas, this could mean derivatives involving the carboxy groups of hyaluronic acid with a semiacetalic structure, while in other cases it could mean alkylated products of hydroxyls.

It is possible, therefore, to define the main object of the present invention as being the total and partial cross-linked esters of hyaluronic acid with polyhydric alcohols of the aliphatic series. In the partial cross-linked esters, there may be carboxy groups esterified with monohydric or polyhydric alcohols of the aliphatic, alicyclic, araliphatic or heterocyclic series, and in the partial esters there may be nonesterified, salified carboxy groups with inorganic or organic bases, with the exception of cross-linked esters obtained by the action of a halomethyloxyrane or of a bisepoxy-compound on hyaluronic acid.

DETAILED DESCRIPTION OF THE INVENTION

The term "hyaluronic acid" is used in literature to mean acidic polysaccharides with different molecular weights consituted by residues of D-glucuronic and N-acetyl-D-glucosamine acids, which occur naturally in cell surfaces, in the basic extracellular substances of the connective tissue of vertebrates, in the synovial fluid of the joints, in the endobulbar fluid of the eye, in human umbilical cord tissue and in cocks' combs. Hyaluronic acid plays an important role in the biological organism, as a mechanical support for the cells of many tissues, such as the skin, tendons, muscles and cartilage and, therefore, it is the main component of the intercellular matrix, but it also plays other important roles in the biological processes, such as the moistening of tissues, lubrication, cell migration, cell functions and differentiation. (See for example A. Balazs et al. in "Cosmetics & Toiletries", Italian edition No. 5/84, pages 8-17).

Hyaluronic acid may be extracted from the above natural tissues, for example from cocks' combs or also from some bacteria. It is possible today to prepare hyaluronic acid also by microbiological methods. The molecular weight of integral hyaluronic acid obtained by extraction is about 8-13 million. However, the molecular chain of this polysaccharide is quite easily degraded by means of various physical and chemical factors for example by mechanical means or under the influence of radiation or hydrolyzing, oxidizing or enzymatic agents. For this reason, even by using the usual purification procedures of original extracts, the degraded fractions obtained have a lower molecular weight (see Balazs et al. cited above).

Hyaluronic acid, its molecular fractions and the respective salts have been used as medicaments and they have been proposed for use in cosmetics (see for example the above article by Balazs et al. and French Patent No. 2478468). As a therapeutic agent, hyaluronic acid and its salts have been used especially in therapy for arthropathies, for example in the veterinary field for the treatment of arthritis in horses [Acta Vet. Scand. 167. 379 (1976)]. As an auxilliary and substitute therapeutic agent for natural organs and tissues, hyaluronic acid and its molecular fractions and their salts have been used in ophthalmic surgery (see for example Balazs et al. in "Modern Problems in Ophthalmology", Vol. 10, 1970, p. 3 - E. B. Strieff, S. Karger eds., Basel, or "Viscosurgery and the Use of Sodium Hyaluronate During Intraocular Lens Implantation", Paper presented at the International Congress and First Film Festival on Intraocular Implantation, Cannes, 1979, and U.S. Pat. No. 4,328,803 with a summary of the literature on uses of HY in ophthalmology, and also U.S. Pat. No. 4,141,973). In EP publication No. 0138572A3 of Apr. 24, 1985 there is a description of a molecular fraction of hyaluronic acid which may be used, for example as a sodium salt, for intraocular and intraarticular injections respectively, suitable as a substitute for the endobulbar fluids in the eye and suitable in therapy for arthropathies.

Hyaluronic acid may be used also as an additive for various polymeric materials used for sanitary and surgical articles, such as polyurethanes, polyesters, polyolefins, polyamides, polysiloxanes, vinyl and acrylic polymers, carbon fibres with the effect of rendering these materials biocompatible. In this case the addition of HY or its salts is effected for example by coating the surface of such materials, or by dispersion in the same or by both these procedures. Such materials may be used to make various sanitary and medical articles, such as cardiac valves, intraocular lenses, vascular clips, pacemakers and similar articles (see U.S. Pat. No. 4,500,676).

The term "hyaluronic acid" is in fact usually used incorrectly, meaning, as has been seen, a whole series of polysaccharides with alternating residues of D-glucuronic and N-acetyl-D-glucosamine acids with varying molecular weights or even the degraded fractions of the same, and it would therefore seem more correct to use the plural term of "hyaluronic acids". The singular term will, however, be used all the same in this description, likewise in the case of the molecular fractions, and, in addition, the abbreviation "HY" will frequently be used in place of this collective term.

It has been found that also the esters of hyaluronic acid with aliphatic, araliphatic, cycloaliphatic or heterocyclic alcohols possess similar and even superior properties to those of the acidic polysaccharide itself and they are even more suitable for the above uses. These esters and a method for their preparation are described in the co-pending U.S. application Ser. No. 881,454 filed on July 2, 1986, which is hereby incorporated by reference. The esters with a high degree of esterification and especially the total esters have, unlike hyaluronic acid, good solubility in organic solvents, for example in dimethylsulfoxide. Thus for example, at room temperature, the benzyl ester of HY dissolves in DMSO in the measure of 200 mg/ml. This solubility in certain organic solvents, together with particular and marked viscous-elastic properties, makes it possible to obtain sanitary, medical and surgical articles which are insoluble in saline and which have the particular desired form: first a solution of the HY ester is prepared in an organic solvent, the very viscous solution is then shaped into the form desired for the finished article and lastly the organic solvent is extracted with another solvent which mixes with the first but in which the HY ester is insoluble. These advantages are also to be found, possibly to an even greater degree, in the cross-linked compounds of the present invention.

The cross-linked esters of the present invention may derive from any polyhydric alcohol of an aliphatic nature, and these derive however preferably from polyhydric alcohols with a maximum of 8 alcohol functions and especially 4 such functions and a maximum of 16 carbon atoms. The term "polyhydric", strictly speaking, generally refers to alcohols having three or more hydroxy groups, while the terms "dihydric" or "glycol" generally refer to alcohols having two hydroxy groups. However, as used herein the term "polyhydric" is meant to encompass alcohols having two or more hydroxy groups. Thus, the "polyhydric" alcohols may be dihydric alcohols, trihydric, tetrahydric, penta and hexahydric alcohols. Of these, special mention should be given to glycerine, the three erythrite isomers, pentaerythrite, the four xylitol isomers and the 10 dulcitol isomers.

In the new esters the "cross-links" may derive from various of the above polyhydric alcohols, however it is preferable to prepare esters in which all the "cross-links" derive from the same polyhydric alcohol.

The most important class of the new esters is the one deriving from dihydric alcohols, that is, from glycols. Such glycols have preferably the aforesaid maximum of 16 carbon atoms, and above all a maximum of 8 carbon atoms and are especially ethyleneglycol, propyleneglycol, butyleneglycol, the glycols deriving from pentane, hexane, heptane, octane and their position isomers. Such glycols may however also have double bonds, for example between one and three double bonds.

The simple ester groups, which may be present in addition to the cross-linked groups, may derive from alcohols of the aliphatic, araliphatic, alicyclic or heterocyclic series and may be substituted or unsubstituted, saturated or unsaturated. Alcohols of the aliphatic series are for example those with a maximum of 34 carbon atoms, which may be saturated or unsaturated and which may possibly also be substituted by other free functional or functionally modified groups, such as amino, hydroxy, aldehydo, keto, mercapto, carboxy groups or by groups deriving from these, such as hydrocarbyl or dihydrocarbylamino groups (here and hereafter the term "hydrocarbyl" should be taken to mean not only monovalent radicals of hydrocarbons e.g. of the $-C_nH_{2n+1}$ type, but also bivalent or trivalent radicals, such as "alkylenes" $-C_nH_{2n}-$ or "alkylidenes" $>C_nH_{2n}$), ether or ester groups, acetal or ketal groups, thioether or thioester groups and esterified carboxy groups or carbamidic groups and substituted carbamidic groups by one or two hydrocarbyl groups, by nitrile groups or by halogens. Of the substituted alcohols it is preferable to choose those with one or two of the abovesaid functions.

Of the aforesaid groups containing hydrocarbyls, these are preferably lower aliphatic radicals, for example alkyls, with a maximum of 6 carbon atoms. Such alcohols may then also be interrupted in the carbon atom chain by heteroatoms, such as oxygen atoms, nitrogen, sulfur. Alcohols of the above group to be used preferentially in the limits of the present invention are those with a maximum of 12 and especially 6 carbon atoms, and those, of the substituted ones, in which the hydrocarbyl radicals in the above said amino, ether, ester, thioether, thioester, acetal, ketal groups represent alkyl groups with a maximum of 4 carbon atoms, and in which in the esterified carboxy groups too, or substituted carbamidic groups, the hydrocarbyl groups are alkyls with the same number of carbon atoms, and in which the amino or carbamidic groups may be alkyleneamine or alkylene-carbamidic groups with a maximum of 8 carbon atoms. Of these alcohols, first and foremost should be mentioned those which are saturated and unsubstituted such as for example methyl, ethyl, propyl, isopropyl alcohols, n-butyl, isobutyl, tert-butyl alcohol, amyl alcohols, pentyl, hexyl, octyl, nonyl and dodecyl alcohols and above all those with a linear chain, such as n-octyl and n-dodecyl alcohols.

Of the substituted alcohols, preferred are the already mentioned glycols, otherwise used for the formation of "cross-links", but also polyhydric alcohols, such as glycerine, the aldehyde alcohols such as tartronic alcohol, carboxy alcohols such as lactic acids, for example α-oxypropionic acid, glycolic acid, malic acid, tartaric acids, citric acid, aminoalcohols, such as aminoethanol, aminopropanol, n-aminobutanol and their dimethyl and diethyl derivatives in the amino function, choline, pyrrolidinylethanol, piperidinylethanol, piperazinylethanol and the corresponding derivatives of n-propyl alcohol or n-butyl alcohol, monothioethylenglycol or its alkyl derivatives, for example the ethyl derivative in the mercapto function. Of the saturate higher aliphatic alcohols, preferred are for example cetyl alcohol and myricyl alcohol, but of special importance for the aims of the present invention are the higher unsaturated alcohols with one or two double bonds, such as especially those contained in many essential oils and having an affinity with terpenes, such as for example citronellol, geraniol, nerol, nerolidol, linalool, farnesol and phytol. Of the unsaturated lower alcohols, allyl alcohol and propargyl alcohol are useful.

Of the araliphatic alcohols, those to be mentioned above all are all those with only one benzene residue and in which the aliphatic chain has a maximum of 4 carbon atoms and in which the benzene residue may be substituted by between 1 and 3 methyl or hydroxy groups or by halogen atoms, especially by chlorine, bromine or iodine, and in which the aliphatic chain may be substituted by one or more functions chosen from the group constituted by free amino or mono or dimethyl groups or by pyrrolidinyl or piperidinic groups. Of these alcohols, above all preferred are benzyl alcohol and phenethyl alcohol.

The alcohols of the cycloaliphatic series (including also cycloaliphatic-aliphatic alcohols) may derive from mono or polycyclic hydrocarbons and may have preferably a maximum of 34 carbon atoms. In the case of substituted alcohols, the substitutes may be those already mentioned for the alcohols of the aliphatic series.

Of the alcohols derived from monoannular cyclic hydrocarbons, special mention should be given to those with a maximum of 12 carbon atoms, the rings having preferably between 5 and 7 carbon atoms, which may be substituted for example by between one and three lower alkyl groups, such as methyl, ethyl, propyl or isopropyl groups. As specific alcohols of this group preferred are cyclohexanol, cyclohexanediol, 1,2,3 cyclohexanetriol and 1,3,5 cyclohexanetriol (phloroglucitol), inositol. The heterocyclic alcohols may be considered as deriving from the above cycloaliphatic or aliphaticcycloaliphatic alcohols if in these the linear or cyclic chains are interrupted by one or more heteroatoms, for example between 1 and 3 heteroatoms chosen from the group formed by $-O-$, $-S-$, $-N=$ and $-NH-$ and in them there may be one or more double bonds, in particular between 1 and 3, thus including also heterocyclic compounds with aromatic structures. They may be simple alcohols, such as furfuryl alcohol or alcohols with a more complicated structure, such as are present in many alkaloid derivatives and in many medicaments.

As already stated, the new cross-linked derivatives of the present invention may be used for all the main applications suitable for hyaluronic acid or its salts or the above esters described in the above co-pending U.S. patent application. As already said, the new derivatives are therefore particularly suitable for the preparation of:
(1) medicaments
(2) Pharmaceutical vehicles for medicaments
(3) cosmetics and vehicles for cosmetics
(4) plastic articles for sanitary, medical and surgical uses
and the present invention includes in particular all these uses.

The type of cross-linked ester is obviously chosen according to the use to which it is to be put. Usually, a high degree of esterification to the point of total esterification of the hyaluronic acid increases its lipophilic character and therefore diminishes its solubility in water. For therapeutic or cosmetic uses it is especially important to regulate the degree of esterification in such a way as to ensure sufficient solubility in water, although it does have good lipophilic qualities compared to hyaluronic acid or its salts. Naturally, the molecular size of the esterifying component itself should be borne in mind, as this usually influences hydrosolubility in an inversely proportional manner. As far as the use of medicaments is concerned, the greater or lesser degree of hydrophilic or lipophilic qualities should be considered in relation to the type of tissue to be treated, for example the skin in the case of dermal medicaments.

The new cross-linked derivatives may be used as therapeutic agents due to the intrinsic property of the hyaluronic component itself, for example as drugs for the treatment of arthritis, both in human and veterinary medicine. In this case they derive from polyhydric aliphatic alcohols with no pharmacological properties or with neglible activity, especially from dihydric alcohols with between 2 and 8 carbon atoms, and the other simple ester groups present possibly also derive from alcohols with no pharmacological action, for example from monohydric aliphatic alcohols with a maximum number of eight carbon atoms. Administration is effected by parenteral route and more precesely by intraarticular route.

Other cross-linked derivatives according to the invention may also derive from alcohols with a pharmacological effect and this is especially true of alcohols from which simple ester groups are derived. They possess properties which are qualitatively similar to those of alcohol, but with a more differentiated range of action, ensuring a more balanced, constant and regular pharmacological action and usually having a marked "retard" effect. Other cross-linked derivatives again may contain simple ester groups of two or more different types of alcohols with or without their own pharmacological action. By suitably dosing the ratio of the different types of alcohols as esterifying components, it is possible to obtain esters with the pharmacological activity of active alcohols without the specific activity of hyaluronic acid having those qualities described above of greater stability and bioavailability with respect to the desired activity and the characteristics of the pharmacologically active alcohols.

In the derivatives described here, deriving from pharmacologically active alcohols, the cross-linked hyaluronic molecule acts basically as a vehicle for the pharmacologically active component, and they may therefore also be included in groups (2) or (3). Since the new cross-linked derivatives act as actual vehicles according to uses (2) and (3), they are preferably also derived from the above said therapeutically inactive polyhydric alcohols, and also possibly ester groups deriving from monohydric alcohols are preferably without any pharmacological action. The active substance is physically mixed with the new derivatives and the resulting medicaments may also contain other ingredients and excipients commonly used in conventional pharmaceutical preparations. In place of an active substance it is possible to have an association of active substances. Particularly interesting are medicaments of this kind in which the new hyaluronic derivatives act as vehicle and containing topically active substances.

The pharmacologically active alcohols to be used for the esterification of carboxy groups not yet cross-linked in the new derivatives, may be, apart from those already listed, aliphatic-cycloaliphatic polycyclic alcohols, such as for example steroids, such as sexual hormones and their synthetic analogues and particularly corticosteroids and their derivatives, such as for example estradiol and its methyl derivatives, ethinyl or propinyl derivatives in position 17, testosterone and its derivatives, such as 17-α-methyl-testosterone, 17-α-ethinyl-testosterone, 1'1,2-dehydro-testosterone, nor-gestrel, 19-nor-testosterone, 19-nor-17-α-methyl-testosterone, anti-hormones such as cyproterone, cortisone, hydrocortisone, dexamethasone, betamethasone, paramethasone, flumethasone, fluocinolone, clobetasol, beclomethasone, alfaxolone, bolasterone. Other therapeutically active alcohols are for example vitamins, such as axerophthol, vitamins $D_2$ and $D_3$, aneurine, lactoflavine, ascorbic acid, riboflavine, thiamine and pantothenic acid. Of the heterocyclic alcohols we also mention atropine, scopolamine, cinchonine, cinchonidine, quinine, morphine, codeine, nalorphine, N-butylscopolammonium bromide, ajmaline; phenylethylamine such as ephedrine, isoproterenol, epinephrine, phenothiazine drugs such as perphenazine, pipotiazine, carphenazine, homofenazine, acetophenazine, fluphenazine, N-hydroxyethylpromethazine chloride; thioxanthene drugs such as flupentixol and clopenthixol; anticonvulsivants such as meprophendiol; antipsychotics such as opipramol; anti-emetics such as oxypendyl; analgesics such as carbetidine and phenoperidine and methadol; hypnotics such as etodroxizine; anorexics such as benzhydrol and diphemethoxidine; minor tranquilizers such as hydroxizine; muscle relaxants such as cinnamedrine, diphylline, mephenesin, methocarbamol, chlorphenesin, 2,2-diethyll,3-propandiol, guaiphenesin, hydrocilamide; coronary vasodilators such as dipyridamole and oxyfedrine; adrenergic blockers such as propanolol, timolol, pindolol, bupranolol, atenolol, metoprolol, practolol; anti-neoplastics such as 6-azauridine, cytarabine, floxuridine; antibiotics such as chloramphenicol, thiamphenicol, erythromycin, oleandomycin, lincomycin; antivirals such as idoxuridine; peripheral vasodilators such as isonicotinyl alcohol; carbonic anhydrase inhibitors such as sulocarbilate; anti-asthmatics and antiinflammatories such as tiaramide; sulphamidics such as 2-p-sulphanylanilinoethanol.

The new cross-linked derivatives described here may of course be used in the same cases as the free alcohols.

One particularly interesting aspect of the present invention is the possibility of preparing more stable drugs than those available up till now. It is possible therefore on the one hand to prepare cross-linked derivatives for use in the indications which are typical of hyaluronic acid itself, for example for intra-articular injections where the cross-linked derivative acts as lubricant: due to the better stability of the derivatives when the hyaluronidase is compared to the free acid, it is possible to obtain a quite notably prolonged action. On the other hand it is possible to obtain drugs with a "retard" action for the above derivatives containing also ester groups deriving from therapeutically active alcohols. In these the pharmacologically active alcohol is very slowly released into the organism by means of esterases. For use according to the above point (4), the new cross-linked derivatives are prepared above all with pharmacologically inert alcohols, for example bivalent saturated aliphatic alcohols, especially those with between 2 and 8 carbon atoms, glycerin and from monovalent alcohols, above all aliphatic alcohols, but also some others of the abovesaid series for partial esterification in the carboxy groups which are not cross-linked. Of this last group, particularly interesting are the unsaturated alcohols, for example those with one or more double bonds such as vinyl or allyl alcohols and their condensed derivatives, such as especially polyvinyl alcohol and glycerin. In this case too it is possible to use mixed esters, according to the particular intended use. Alicyclic alcohols are also useful, for example derived from cyclopentane and cyclohexane and from their derivatives substituted by inferior alkyl groups, for example alkyls with between 1 and 4 carbon atoms, especially by methyl groups.

For cosmetic use it is preferable to use crosslinked derivatives with esterified groups substantially identical to those listed above for the use of sanitary, medical and surgical articles. Also to be considered are terpene alcohols, such as those mentioned above, especially odoriferous alcohols for the preparation of perfumes and scented creams.

In all the cross-linked derivatives according to the present invention the carboxy groups not "cross-linked" or not esterified may be free or salified. The salts may have inorganic bases, for example alkaline metals such as potassium and particularly sodium and ammonium, and alkaline earth metals such as calcium, or magnesium and aluminium salts, or may have organic bases, especially azotized bases and therefore aliphatic, araliphatic, cycloaliphatic or heterocyclic amines. These salts may derive from therapeutically acceptable but inactive amines, or from amines with a therapeutic action.

Of the former, consideration is to be given above all to the aliphatic amines, for example mono-, di and trialkylamines with alkyl groups with a maximum of 18 carbon atoms or arylalkylamines with the same number of carbon atoms in the aliphatic part and where aryl means a benzene group possibly substituted be between 1 and 3 methyl groups or halogen atoms or hydroxy groups. The biologically inactive bases for the formation of the salts may also be cyclic such as monocyclic alkylenamines with cycles of between 4 and 6 carbon atoms, possibly interrupted in the cycle by heteroatoms chosen from the group formed by nitrogen, oxygen and sulfur, such as piperidine, piperazine or morpholine, or may be substituted for example by amino or hydroxy functions, such as aminoethanol, ethylendiamine, ephedrine, or choline.

It is also possible to form the quaternary ammonium salts of partial esters, for example tetraalkylammonium salts with the above said number of carbon atoms and preferably salts of the same type in which the fourth alkyl group has between 1 and 4 carbon atoms, for example a methyl group.

Those biologically active amines whose therapeutic action may be put to use, include azotated and basic drugs such as those included in the following groups: alkaloids, peptides, phenothiazine, benzodiazepine, thioxantene, hormones, vitamins, anticonvulsivants, antipsychotics, antiemetics, anesthetics, hypnotics, anorexics, tranquillizers, muscle-relaxants, coronary vasodilators, antineoplastics, antibiotics, antibacterials, antivirals, antimalarials, carbonic anhydrase inhibitors, nonsteroid anti-inflammatories, vasoconstrictors, cholinergic agonists, cholinergic antagonists, adrenergic agonists, adrenergic blockers, narcotic antagonists.

All those drugs with the basic azotated groups listed in the invention can be mentioned as examples regarding the use of the esters. Salification of the nonesterified carboxy groups with therapeutically active bases may substitute or integrate the vehicling function of the new cross-linked derivatives obtained by esterification with therapeutically active alcohols and therefore represents another particlular case of the use of the new compounds as therapeutic vehicles according to point (2): the active bases are vehicled both by the neutral salts obtainable by addition of the basic stoichiometric quantity, both from the basic salts obtainable by addition of an excess of base or of those acids obtainable by addition of a basic defect.

The new hyaluronic derivatives according to the present invention are particularly useful since they are medicaments for local or topical use, especially in ophthalmology, where they show particular compatibility with the corneal epithelium and are therefore very well tolerated, with no sensitization effects. Furthermore, when the medicaments are administered in the form of concentrated solutions with elastic-viscous characteristics or in solid form, it is possible, on the corneal epithelium, to obtain homogenous, stable and perfectly transparent films which are also perfectly adhesive, guaranteeing prolonged bioavailability of the drug and which therefore constitute excellent preparations with a retard effect.

These ophthalmic medicaments are of exceptional value especially in the veterinary field, considering that there are at present no veterinary specialities containing chemical agents. Indeed, products intended for human use are used on animals, and these cannot always guarantee a specific range of action and are sometimes unsuitable for application in the conditions under which they are to be administered. For example, this is the case of therapy for infective keratoconjunctivitis, pink eye or IBK, an infection which usually affects cattle, sheep and goats. Presumably, specific etiological factors exist for these three species and more particularly: in cattle the main micro-organism involved seems to be Moraxella bovis (even though other agents of viral origin are not to be excluded, such as the Rhinotracheitis virus, in sheep Mycoplasma, Rickettsia and Chlamydia, in goats Rickettsia). The disease presents itself in acute form and tends to spread rapidly: in the initial stages the symptomatology is characterised by blepharospasm and excessive lacrimation, followed by purulent discharge, conjunctivitis and keratitis, often associated with fever, a reduction in appetite and milk production. Particularly serious are the corneal lesions which in the final stages may even cause perforation of the cornea itself. The clinical course varies from a few days to several weeks.

A vaste range of therapies involving chemical agents are used, administered both by topical route (often associated with steroid anti-inflammatory agents), and systemic route, such as: tetracycline, such as oxytetracycline, penicillin, such as cloxacillin and benzyl penicillin, sulphamidics, polymixin B (associated with miconazole and prednisolone), chloramphenicol, tylosin and chloromycetin. Topical treatment of the disease, despite its apparent simplicity, is still an open problem, since with the ocular preparations used until now it has not been possible for one reason or another to obtain concentrations of therapeutically effective antibiotics or sulphamidics in the lachrymal secretion. This fact is fairly understandable in the case of solutions, considering the predominantly inclined position of the head in the abovesaid animals, but it is also true of semisolid medicaments, since the excipients commonly used in the same do not have the necessary qualities to adhere to the surface of the cornea. This is because they do not usually have a sufficiently high concentration of active substance and cannot obtain perfect distribution of the same (presence of a distribution gradient). These drawbacks to conventional colliriums for ophthalmics have for example been described by Slatter et al. in "Austr.vet.J.," 1982, 59 (3), pp. 69-72. With the esters of the present invention these difficulties can be overcome. Indeed, the presence of the hyaluronic ester as a vehicle in ophthalmic drugs allows for the formulation of excellent preparations with no concentration gradient of active substance and being therefore perfectly homogenous, transparent and adhesive to the corneal epithelium, with no sensitization effects and with the active substance acting as an excellent vehicle, possibly also with a retard effect. Medicaments containing the new derivatives which may be used in ophthalmic treatments mainly concern miotic, wound healing, anti-inflammatory and anti-microbial/antibiotic effects. Some examples of antibiotic substances are: basic and nonbasic antibiotics, for example aminoglucosidics, macrolidics, tetracycline and peptides, such as for example gentamycin, neomycin, streptomycin, dihydrostreptomycin, kanamycin, amikacin, tobramycin, spectinomycin, erythromycin, oleandomycin, carbomycin, spiramycin, oxytetracycline, rolitetracycline, bacitracin, polymyxin B, gramicidin, colistin, chloramphenicol, lincomycin, vancomycin, novobiocin, ristocetin, clindamycin, amphotericin B, griseofulvin, nystatin and possibly their salts, such as sulphates or nitrates, or associations of the same either among themselves or with other active principles, such as for example those mentioned below.

Other ophthalmic drugs to be used to advantage according to the present invention are: other anti-infectives such as diethylcarbamazine, mebendazole, sulphamidics such as sulfacetamide, sulfadiazine, sulfisoxazole; antivirals and antitumorals such as iododeoxyuridine, adenine arabinoside, trifluorothymidine, acyclovir, ethyldeoxyuridine, bromovinyldeoxyuridine, 5-iodo-5'-amino-2',5'-dideoxyuridine; steroid anti-inflammatories, such as dexamethasone, hydrocortisone, prednisolone, fluorometholone, medrysone and possibly their esters, for example phosphoric acid esters; non steroid anti-inflammatories such as indomethacin, oxyphenbutazone, flurbiprofen; wound healers such as epidermal growth factor EGF; local anesthetics, such as Benoxinate, proparacaine and possibly their salts; cholinergic agonist drugs such as pilocarpine, methacholine, carbamylcholine, aceclidine, physostigmine, neostigmine, demecarium and possibly their salts; cholinergic blocker drugs such as atropine and its salts; adrenergic agonist drugs such as noradrenaline, adrenalin, naphazoline, methoxamine and possibly their salts; adrenergic blocker drugs such as propanolol, timolol, pindolol, bupranolol, atenolol, metoprolol, oxprenolol, practolol, butoxamine, sotalol, butadrin, labetalol and possibly their salts.

Examples of active substances to be used on their own or in association among themselves with other active principles in dermatology are: therapeutic agents such as anti-infective agents, antibiotics, antimicrobials, anti-inflammatories, cytostatics, cytotoxics, antivirals, anesthetics, and preventive agents, such as sun shields, deodorants, antiseptics and disinfectants.

From the examples quoted for ophthalmology and dermatology, it is reasonable to assume by analogy which are the medicaments according to the present invention suitable for use in the various fields of medicine, such as for example otolaryngology, gynecology, angiology, neurology or any other type of pathology of the internal organs which may be treated by local topical applications, for example by rectal action. It is of course possible to prepare associations of therapeutically active substances with the new derivatives according to the present invention, suitable for parenteral administration. In the latter case, to obtain aqueous solutions for injection, hyaluronic derivatives with a low level of cross-linking and/or esterification should be chosen. Derivatives which are only slightly, or not at all soluble in water, can be used to make associations containing the active substances for administration in solutions of organic substances, for example oily solutions.

The medicaments of the type described here for topical use may be in solid form, such as freezedried powders containing only the two components as a mixture or separately. Such solid form medicaments, on contact with the epithelium to be treated, form more or less concentrated solutions according to the nature of the particular epithelium having the same characteristics as the solutions previously prepared in vitro and which represent another particlularly interesting aspect of the present invention. Such solutions are preferably in distilled water or sterile saline and contain prefereably no other pharmaceutical vehicle besides the hyaluronic ester or one of its salts. The concentrations of such solutions may also vary within wide limits, for example between 0.01 and 75% both for each of the of the two components taken separately, and for their mixtures or salts. Particular preference is given to solutions with pronounced elastic viscous properties, for example with a content of between 10% and 90% of the medicament or of each of its components. Particularly important are medicaments of this type, both in an anhydrous form (freeze-dried powder) or as concentrated solutions or diluted in water or saline, possibly with the addition of additive or auxilliary substances, such as in particular disinfectant substances or mineral salts acting as vehicle or others, for ophthalmic use.

Of the medicaments of the invention it is preferable to choose, as the case may be, those with a degree of acidity suitable for the environment to which they are to be applied, that is, with a physiologically tolerable pH. The pH, for example in the above salts of the hyaluronic acid esters with a basic active substance, may be adjusted by suitably regulating the quantity of polysaccharide, of its salts and of the basic substance itself. Thus, for example, if the acidity of a salt of a hyaluronic ester with a basic substance is too high, the excess of free acid groups is neutralized with the above said inorganic bases, for example with sodium or potassium or ammonium hydrate.

METHODS OF PREPARING HY ESTERS OF THE INVENTIONS

The new cross-linked derivatives of the present invention may be prepared by methods per se known for the esterification of carboxy acids, for example for treatment of free hyaluronic acid with the above polyhydric alcohols in the presence of catalysts, such as strong inorganic acids or acid-type ionic exchangers, or with an etherifying agent able to introduce the desired alcohol residue in the presence of inorganic or organic bases. As etherifying agents it is possible to use those named in literature, such as especially the esters of various inorganic acids or organic sulfonic acids, such as hydrogen acids, that is the alkyl halogenide, such as methyl iodide or other alkyl groups which are at the base of the above bivalent alcohols.

The reaction may be effected in a suitable solvent, for example an alcohol, preferably the one corresponding to the alkyl group to be introduced into the carboxy group, but may also be effected in non-polar solvents such as ketones, ethers, such as dioxane or aprotic solvents, such as dimethylsulfoxide. As a base, it is possible to use for example a hydrate of an alkaline metal, alkaline earth metal or magnesium or oxide of silver or a basic salt of one of these metals, such as carbonate, and, of the organic bases, a tertiary azotized base, such as pyridine or collidine. Instead of the base, a basic-type ion exchanger may be used.

Another esterification method involves metal salts or salts with organic azotized bases, for example ammonium or ammonium substitute salts. Preferably, the salts of alkaline or alkaline earth metals should be used, but any other metal salt may also be used. The etherifying agents are also in this case those mentioned above and the same is true of the solvents. Preferably, aprotic solvents should be used, for example dimethylsulfoxide and dimethylformamide. These esterification methods may of course also be used to prepare the simple esters described above.

According to a new and original procedure described in the above co-pending U.S. application and regarding the simple esters of hyaluronic acid, these may be prepared to advantage, starting with the quaternary ammonium salts of hyaluronic acid with an etherifying agent in an aprotic solvent, such as dialkylsulfoxides, dialkylcarboxylamides, such as in particular lower alkyl dialkylsulfoxides, above all dimethylsulfoxide, and lower alkyl dialkylamides of inferior aliphatic acids, such as dimethyl or diethyl formamide or dimethyl or diethylacetamide. The reaction is effected preferably at a temperature range of between about 0° and 100°, and especially between about 25° and 75°, for example at about 30°. Esterification is effected preferably by gradually adding the esterifying agent to the above ammonium salt dissolved an one of the solvents mentioned, for example in dimethylsulfoxide.

The same method can be used to prepare the typical cross-linked esters of the present invention, that is, the bridge bonds between two carboxy groups are easily formed by etherifying substances deriving from the above polyhydric alcohols on the quaternary ammonium salts of hyaluronic acid. As starting quaternary ammonium salts, it is preferable to use an inferior ammonium tetraalkylates, the alkyl groups having preferably between 1 and 6 carbon atoms. As a first choice, tetrabutylammonium hyaluronate should be used. These quaternary ammonium salts can be Prepared by reacting a metal salt of hyaluronic acid, preferably one of those mentioned above, especially sodium or potassium salt, in aqueous solution with a sulfonic resin salified with the quaternary ammonium base. Tetraalkylammonium hyaluronate can be obtained by freeze-drying the eluate.

The tetraalkylammonium hyaluronates deriving from lower alkyls, especially alkyls with between 1 and 6 carbon atoms, are new and form another object of the present invention. Unexpectedly, such salts have proved to be soluble in the above aprotic solvents, and esterification of hyaluronic acid according to the above new procedure is therefore particularly easy and gives abundant yields. It is, therefore, only by such a procedure that it is possible to exactly dose the number of hyaluronic acid carboxy groups to be esterified.

One variation of the previously specified procedure consists in reacting the potassium or sodium salt of hyaluronic acid, suspended in a suitable solvent such as dimethylsulfoxide, with a suitable etherifying agent in the presence of a catalyzing quantity of quaternary ammonium salt, such as tetrabutylammonium iodide. For the preparation of the new esters according to the present invention, hyaluronic acids of any origin may be used, for example the acids extracted from the above natural starting materials, for example from cocks' combs. The preparation of such acids is described in literature: preferably, purified hyaluronic acids should be used. According to the invention, it is preferable to use hyaluronic acids comprising the molecular fractions of the integral acids obtained directly by extraction of the organic materials with molecular weights which may vary greatly, for example between about 90%–80% and 0,2% of the molecular weight of the integral acid, preferably between 5% and 0,2%. These fractions may be obtained by various procedures described in literature, and that is, by hydrolizing or oxidizing or enzymatic agents or physical procedures, for example mechanical procedures or by irradiation, and often therefore, primordial extracts are formed during these same purification procedures (see for example the above mentioned article by Balazs et al. in "Cosmetics & Toiletries"). The separation and purification of the molecular fractions obtained is effected for example by known techniques, for example by molecular filtration.

One purified HY fraction suitable for use according to the invention is for example the one named "non-inflammatory sodium hyaluronate-NIF-NaHA described by Balazs in the leaflet "Healon" - A guide to its use in Ophthalmic Surgery - D. Miller & R. Stegmann, eds. John Wiley & Sons N.Y. 81983: p.5. Particulary important as starting materials for the esters of the present invention are two purified fractions obtainable from hyaluronic acid, for example the type extracted from cocks' combs, known by the names of "Hyalastine" and "Hyalectin". The fraction Hyalastine has an average molecular weight of between about 50,000 and 100,000 while the fraction Hyalectin has an average molecular weight of between about 500,000 and 730,000. One fraction combined with these two fractions has also been isolated and characterized as having an average molecular weight of between about 250,000 and 350,000. This combined fraction may be obtained giving a yield of total hyaluronic acid equal to 80% of the amount available in the particular starting material, while the fraction Hyalectin can be obtained with a yield of 30% and the fraction Hyalastine with a yield of 50% of the starting HY. The preparation of these fractions is described in Examples 38 and 40.

In the new cross-linked derivatives of hyaluronic acid the nonesterified carboxy groups may be free or salified or partially salified and various different types of cross-linked products are therefore obtained. That is, those in which the remaining carboxy groups are free or salified, those in which the remaining carboxy groups are totally or partially esterified and in the latter the remaining groups may in turn be free or salified. Thus, a whole range of products is available, varying in their physical properties and especially regarding their degree of acidity and visco-elastic properties and their ability to form gels. The number of acid groups to be kept free may be important for the preparation of medicaments with a particular pH.

Preparation of the salts of the new derivatives can be carried out in the known manner, for example by reacting on the hyaluronic derivative the calculated basic quantity of alkaline hydrates for example or basic salts of alkaline metals, such as carbonates or bicarbonates. It is possible for example to first prepare aqueous solutions of the hyaluronic derivative and of the base, freeing such substances from the aqueous solutions of their salts with suitable ionic exchangers, pooling the two solutions at a low temperature, for example between 0° and 20°; if the salt thus obtained is easily soluble in water it is freeze-dried, while the less soluble salts may be separated by centrifugation or filtration or decanting and possibly then dried. In the case of the organic bases, to be vehicled with the new cross-linked derivatives, the medicaments obtained as salts of such bases with the new derivatives may be neutral, acid or basic according to whether stoichiometric quantities are added, or whether there is a basic defect or excess.

According to a particular aspect of the invention it is possible to prepare medicaments of the above type starting with the previously isolated salts and possibly purified, in an anhydrous state, such as amorphous powders, which on contact with the tissue to be treated constitute a concentrated aqueous solution of a gelatinous character, viscous consistency and with elastic properties. These qualities are maintained also at stronger dilutions and may be used in place of the above anydrous salts, more or less concentrated solutions in water or saline, possibly with the addition of other excipients or additives, such as other mineral salts to regulate the PH and osmotic pressure. It is of course also possible to use the salts to make gels, inserts, creams or ointments, including other excipients or ingredients used in traditional formulations of these pharmaceutical preparations.

Of the new products of the present invention the esters described above and their salts and those featuring in the following illustrative Examples should be placed in particular evidence.

The present invention also includes modifications of the preparation procedures of the new esters and of their salts, in which a procedure is interrupted at any stage or in which the procedure starts with an intermediate compound and the remaining stages are then effected, or in which the starting products are formed in situ.

The invention is illustrated by the following Examples, without them limiting its range, in which DMSO means dimethylsulfoxide. The products described in the Examples comprise cross-linked esters according to the invention, having a percentage of the hyaluronic acid carboxyls esterified with a polyhydric alcohol, and having the remaining carboxyls salified and/or esterified with a monohydric alcohol. Table 1 lists the various products according to Examples 1-37 describing the number of carboxyls esterified with the specified polyhydric alcohol, and the number of carboxyls salified with sodium and/or esterified with the specified monohydric alcohol.

EXAMPLE 1

Preparation of hyaluronic acid (HY) partially esterified with ethanol and partially cross-linked with 1-3 propandiol 6.21 g of tetrabutylammonium salt of HY (10 mEq) are solubilized in 248 ml of DMSO at 25° C. under rigorously damp-free conditions, in nitrogen atmosphere and away from light. 0.078 g of ethyl iodide are added (0.5 mM) and the solution is agitated for 15 hr at 30° C. 0.074 g of 1-3 diiodopropane are added (0.25 mM, corresponding to 0.5 mEq) and after homogenization the solution is kept at 30° C. for 24 hr.

For conversion of the residue tetrabutylammonium carboxy groups into sodium salt, to the resulting solution is added 2.5 g of NaCl dissolved in 100 ml of distilled $H_2O$, while cooling it from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, then vacuum-dried.

4.01 g of the compound featured in the title are obtained.

Ethoxyl determination is carried out according to the method of Cundiff et al. (Anal. Biochem. 33, 1028, 1961) and shows a content of 0.56% w/w as ethanol (theoretical: 0.574). Analysis of the total ester groups is carried out by saponification reaction with an excess quantity of NaOH 0.1N at 50° C. for 30 min. The excess is determined by titration with HCl 0.1N using phenolphthalein as indicator In this way it is possible to determine a total ester group content equal to 0.24 mEq/g (theoretical: 0.25).

EXAMPLE 2

Preparation of hyaluronic acid (HY) partially esterified with ethanol and partially cross-linked with 1-3 propandiol 6.21 g of tetrabutylammonium salt of HY (10 mEq) are solubilized in 248 ml di DMSO a 25° C. in rigourously damp-free conditions, in nitrogen atmosphere and away from light. 0.078 g of ethyl iodide are added (0,5 mM) and the solution is agitated for 15 hr at 30° C. 0.148 g of 1-3 diiodopropane are added (0.5 mM, corresponding to 1 mEq) and after homogenization the solution is kept at 30° C. for 24 hr.

For conversion of the residue tetrabutylammonium carboxy groups into sodium salt, to the resulting solution is added 2.5 g of NaCl dissolved in 100 ml of distilled $H_2O$, while cooling it from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, then vacuum-dried.

3.99 g of the compound featured in the title are obtained.

Ethoxyl determination is carried out according to the method of Cundiff et al. and shows a content of 0.56% w/w as ethanol (theoretical: 0.574). Analysis of the total ester groups is carried out by saponification reaction with an excess quantity of NaOH 0.1N at 50° C. for 30 min. The excess is determined by titration with HCl 0.1N using phenolphthalein as indicator. In this way it is possible to determine a total ester group content equal to 0.36 mEq/g (theoretical 0.374).

EXAMPLE 3

Preparation of hyaluronic acid (HY) partially esterified with ethanol and partially cross-linked with 1-3 propandiol 6.21 g of tetrabutylammonium salt of HY (10 mEq) are solubilized in 248 ml di DMSO at 25° C. in rigourously damp-free conditions, in nitrogen atmosphere and away from light. 0.078 g of ethyl iodide are added (0.5 mM) and the solution is agitated for 15 hr at 30° C. 0.296 g of 1-3 diiodopropane are added (1 mM, corresponding to 2 mEq) and after homogenization the solution is kept at 30° C. per 24 hr.

For conversion of the residue tetrabutylammonium carboxy groups into sodium salt, to the resulting solution is added 2.5 g of NaCl dissolved in 100 ml of distilled $H_2O$, while cooling it from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, then vacuum-dried.

3.98 g of the compound featured in the title are obtained.

Ethoxyl determination is carried out according to the method of Cundiff et al. and shows a content of 0.56% w/w as ethanol (theoretical: 0.574). Analysis of the total ester groups is carried out by saponification reaction with an excess quantity of NaOH 0.1N at 50° C. for 30 min. The excess is determined by titration with HCl 0.1N using pheonlphthalein as indicator. In this way it is possible to determine a total ester group content equal to 0.61 mEq/g (theoretical 0.623).

EXAMPLE 4

Preparation of hyaluronic acid (HY) partially esterified with ethanol and partially cross-linked with 1-3 propandiol 6.21 g of tetrabutylammonium salt of HY (10 mEq) are solubilized in 248 ml of DMSO at 25° C. under rigourously damp-free conditions, in nitrogen atmosphere and away from light. 0.156 g of ethyl iodide are added (1mM) and the solution is agitated for 15 hr at 30° C. 0.296 g of 1-3 diiodopropane are added (1mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled H$_2$O, while it is cooled from the outside with a bath of H$_2$O/ice.

500 ml of acetone are added, the precipitate is separated by filtration, washed 3 times with 100 ml of acetone/H$_2$O 5:1 and 3 times with 100 ml of pure acetone, and then vacuum dried.

4.00 g of the compound featured in the title are obtained.

Ethoxyl determination is carried out according to the method of Cundiff et al. and shows a content of 1.08% w/w as ethanol (theoretical: 1.15). Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 0.735 mEq/g (theoretical 0.747)

EXAMPLE 5

Preparation of hyaluronic acid (HY) partially esterified with ethanol and partially cross-linked with 1-3 propandiol 6.21 g of tetrabutylammonium salt of HY (10 mEq) are solubilized in 248 ml of DMSO at 25° C. in absolutely dry conditions, in nitrogen atmosphere and away from light. 0.312 g of ethyl iodide are added (2 mM) and the solution is agitated for 15 hr at 30° C. 0.296 g of 1-3 diiodopropane are added (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled H$_2$O, while it is cooled from the outside with a bath of H$_2$O/ice.

500 ml of acetone are added, the precipitate is separated by filtration, washed 3 times with 100 ml of acetone/H$_2$O 5:1 and 3 times with 100 ml of pure acetone, and then vacuum dried.

4.01 g of the compound featured in the title are obtained.

Ethoxyl determination is carried out according to the method of Cundiff et al. and shows a content of 2.18% w/w as ethanol (theoretical: 2.29). Total ester group analysis is carried out by saponification reaction with an excess quantity of NaOH 0.1N a 50° C. for 30 min. The excess is determined by titration with HCl 0.1N using phenolphthalein as an indicator. It is thus possible to determine a total ester group content of 0.98 mEq/g (theoretical 0.995).

EXAMPLE 6

Preparation of hyaluronic acid (HY) partially esterified with ethanol and partially cross-linked with 1-3 propandiol 6.21 g of tetrabutylammonium salt of HY (10 mEq) are solubilized in 248 ml of DMSO at 25° C. in rigourously damp-free conditions, in nitrogen atmosphere and away from light. 0.624 g of ethyl iodide are added (4 mM) and the solution is agitated for 15 hr at 30° C. 0.296 g of 1-3 diiodopropane are added (1mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled H$_2$O, while it is cooled from the outside with a bath of H$_2$O/ice.

500 ml of acetone are added, the precipitate is separated by filtration, washed 3 times with 100 ml of acetone/H$_2$O 5:1 and 3 times with 100 ml of pure acetone, and then vacuum dried.

4.00 g of the compound featured in the title are obtained.

Ethoxyl determination is carried out according to the method of Cundiff et al. and shows a content of 4.5% w/w as ethanol (theoretical: 4.57). Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 1.43 mEq/g (theoretical: 1.49).

EXAMPLE 7

Preparation of hyaluronic acid (HY) partially esterified with ethanol and partially cross-linked with 1-3 propandiol 6.21 g of tetrabutylammonium salt of HY (10 mEq) are solubilized in 248 ml of DMSO at 25° C. in absolutely dry conditions, in nitrogen atmosphere and away from light. 0.934 g of ethyl iodide are added (6 mM) and the solution is agitated for 15 hr at 30° C. 0.296 g of 1-3 diiodopropane are added (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled H$_2$O, while it is cooled from the outside with a bath of H$_2$O/ice.

500 ml of acetone are added, the precipitate is separated by filtration, washed 3 times with 100 ml of acetone/H$_2$O 5:1 and 3 times with 100 ml of pure acetone, and then vacuum dried.

4.03 g of the compound featured in the title are obtained.

Ethoxyl determination is carried out according to the method of Cundiff et al. and shows a content of 6.74% w/w as ethanol (theoretical: 6.83). Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 1.96 mEq/g (theoretical: 1.98).

EXAMPLE 8

Preparation of hyaluronic acid (HY) partially esterified with ethanol and partially cross-linked with 1-3 propandiol 6.21 g of tetrabutylammonium salt of HY (10 mEq) are solubilized in 248 ml of DMSO a 25° C. in absolutely dry conditions, in nitrogen atmosphere and away from light. 1.170 g of ethyl iodide are added (7.5 mM) and the solution is agitated for 15 hr at 30° C. 0.296 g of 1-3 diiodopropane are added (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

4.02 g of the compound featured in the title are obtained.

Ethoxyl determination is carried out according to the method of Cundiff et al. and shows a content of 8.46% w/w as ethanol (theoretical: 8.52). Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 2.28 mEq/g (theoretical: 2.34).

EXAMPLE 9

Preparation of hyaluronic acid (HY) partially esterified with ethanol and partially cross-linked with 1-3 propaniol 6.21 g of tetrabutylammonium salt of HY (10 mEq) are solubilized in 248 ml of DMSO at 25° C. in absolutely dry conditions, in nitrogen atmosphere and away from light. 0.624 g of ethyl iodide are added (4 mM) and the solution is agitated for 15 hr at 30° C. 0.592 g of 1-3 diiodopropane are added (2 mM, corresponding to 4 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while cooling it from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

3.99 g of the compound featured in the title are obtained.

Ethoxyl determination is carried out according to the method of Cundiff et al. and shows a content of 4.42% w/w as ethanol (theoretical: 4.57). Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 1.96 mEq/g (theoretical: 1.99).

EXAMPLE 10

Preparation of hyaluronic acid (HY) partially esterified with ethanol an partially cross-linked with 1-4 butanediol 6.21 g of tetrabutylammonium salt of HY (10 mEq) are solubilized in 248 ml of DMSO at 25° C. in absolutely dry conditions, in nitrogen atmosphere and away from light. 0.312 g of ethyl iodide are added (2 mM) and the solution is agitated for 15 hr at 30° C. 0.310 g of 1-3 diiodobutane are added (1mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

4.02 g of the compound featured in the title are obtained.

Ethoxyl determination is carried out according to the method of Cundiff et al. and shows a content of 2.3% w/w as ethanol (theoretical: 2.28). Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 0.97 mEq/g (theoretical: 0.99).

EXAMPLE 11

Preparation of hyaluronic acid (HY) partially esterified with ethanol and partially cross-linked with 1-4 butanediol 6.21 g of tetrabutylammonium salt of HY (10 mEq) are solubilized in 248 ml of DMSO at 25° C. in absolutely dry conditions, in nitrogen atmosphere and away from light. 0.624 g of ethyl iodide are added (4 mM) and the solution is agitated for 15 hr at 30° C. 0.310 g of 1-4 diiodobutane are added (1mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

3.95 g of the compound featured in the title are obtained.

Ethoxyl determination is carried out according to the method of Cundiff et al. and shows a content of 2.25% w/w as ethanol (theoretical: 2.28). Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total determine a total ester group content of 1.41 mEq/g (theoretical: 1.48).

EXAMPLE 12

Preparation of hyaluronic acid (HY) partially esterified with ethanol and partially cross-linked with 1-4 butanediol 6.21 g of tetrabutylammonium salt of HY (10 mEq) are solubilized in 248 ml of DMSO at 25° C. in absolutely dry conditions, in nitrogen atmosphere and away from light. 0.936 g of ethyl iodide are added (6 mM) and the solution is agitated for 15 hr at 30° C. 0.310 g of 1-4 diiodobutane are added (1mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

3.98 g of the compound featured in the title are obtained.

Ethoxyl determination is carried out according to the method of Cundiff et al. and shows a content of 6.69% w/w as ethanol (theoretical: 6.81). Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 1.91 mEq/g (theoretical: 1.97).

EXAMPLE 13

Preparation of hyaluronic acid (HY) partially esterified with ethanol and partially cross-linked with 1-6 hexanediol 6.21 g of tetrabutylammonium salt of HY (10 mEq) are solubilized in 248 ml of DMSO at 25° C. in absolutely dry conditions, in nitrogen atmosphere and away from light. 0.312 g of ethyl iodide are added (2 mM) and the solution is agitated for 15 hr at 30° C. 0.244 g of 1-6 dibromohexane are added (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

4.05 g of the compound featured in the title are obtained.

Ethoxyl determination is carried out according to the method of Cundiff et al. and shows a content of 2.18% w/w as ethanol (theoretical: 2.27). Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 0.96 mEq/g (theoretical 0.985).

EXAMPLE 14

Preparation of hyaluronic acid (HY) partially esterified with ethanol and partially cross-linked with 1-6 hexanediol 6.21 g of tetrabutylammonium salt of HY (10 mEq) are solubilized in 248 ml of DMSO at 25° C. in absolutely dry conditions, in nitrogen atmosphere and away from light. 0.624 g of ethyl iodide are added (4 mM) and the solution is agitated for 15 hr at 30° C. 0.244 g of 1-6 dibromohexane are added (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

4.02 g of the compound featured in the title are obtained.

Ethoxyl determination is carried out according to the method of Cundiff et al. and shows a content of 4.46% w/w as ethanol (theoretical: 4.52). Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 1.43 mEq/g (theoretical: 1.47).

EXAMPLE 15

Preparation of hyaluronic acid (HY) partially esterified with ethanol and partially cross-linked with 1-6 hexanediol 6.21 g of tetrabutylammonium salt of HY (10 mEq) are solubilized in 248 ml of DMSO at 25° C. in absolutely dry conditions, in nitrogen atmosphere and away from light. 0.934 g of ethyl iodide are added (6 mM) and the solution is agitated for 15 hr at 30° C. 0.244 g of 1-6 dibromohexane are added (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

4.00 g of the compound featured in the title are obtained.

Ethoxyl determination is carried out according to the method of Cundiff et al. and shows a content of 6.68% w/w as ethanol (theoretical: 6.76). Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 1.91 mEq/g (theoretical: 1.96).

EXAMPLE 16

Preparation of hyaluronic acid (HY) partially esterified with ethanol and partially cross-linked with 1-8 octanediol 6.21 g of tetrabutylammonium salt of HY (10 mEq) are solubilized in 248 ml of DMSO at 250° C. in absolutely dry conditions, in nitrogen atmosphere and away from light. 0.078 g of ethyl iodide are added (0.5 mM) and the solution is agitated for 15 hr at 30° C. 0.068 g of 1-8 dibromooctane are added (0.25 mM, corresponding to 0.5 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

3.99 g of the compound featured in the title are obtained.

Ethoxyl determination is carried out according to the method of Cundiff et al. and shows a content of 0.54% w/w as ethanol (theoretical: 0.571). Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 0.23 mEq/g (theoretical: 0.25).

EXAMPLE 17

Preparation of hyaluronic acid (HY) partially esterified with ethanol and partially cross-linked with 1-8 octanediol 6.21 g of tetrabutylammonium salt of HY (10 mEq) are solubilized in 248 ml of DMSO at 25° C. in absolutely dry conditions, in nitrogen atmosphere and away from light. 0.078 g of ethyl iodide are added (0.5 mM) and the solution is agitated for 15 hr at 30° C. 0.136 g of 1-8 dibromooctane are added (0.5 mM, corresponding to 1 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

3.97 g of the compound featured in the title are obtained.

Ethoxyl determination is carried out according to the method of Cundiff et al. and shows a content of 0.55% w/w as ethanol (theoretical: 0.569. Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 0.35 mEq/g (theoretical: 0.37).

EXAMPLE 18

Preparation of hyaluronic acid (HY) partially esterified with ethanol and partially cross-linked with 1-8 octanediol 6.21 g of tetrabutylammonium salt of HY (10 mEq) are solubilized in 248 ml of DMSO at 25° C. in absolutely dry conditions, in nitrogen atmosphere and away from light. 0.078 g of ethyl iodide are added (0.5 mM) and the solution is agitated for 15 hr at 30° C. 0.272 g of 1-8 dibromooctane are added (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

4.05 g of the compound featured in the title are obtained.

Ethoxyl determination is carried out according to the method of Cundiff et al. and shows a content of 0.55% w/w as ethanol (theoretical: 0.564. Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 0.60 mEq/g (theoretical: 0.61).

EXAMPLE 19

Preparation of hyaluronic acid (HY) partially esterified with ethanol and partially cross-linked with 1-8 octanediol 6.21 g of tetrabutylammonium salt of HY (10 mEq) are solubilized in 248 ml of DMSO at 25° C. in absolutely dry conditions, in nitrogen atmosphere and away from light. 0.156 g of ethyl iodide are added (1 mM) and the solution is agitated for 15 hr at 30° C. 0.272 g of 1-8 dibromooctane are added (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

4.01 g of the compound featured in the title are obtained.

Ethoxyl determination is carried out according to the method of Cundiff et al. and shows a content of 1.09% w/w as ethanol (theoretical: 1.13. Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 0.70 mEq/g (theoretical: 0.73).

EXAMPLE 20

Preparation of hyaluronic acid (HY) partially esterified with ethanol and partially cross-linked with 1-8 octanediol 6.21 g of tetrabutylammonium salt of HY (10 mEq) are solubilized in 248 ml of DMSO at 25° C. in absolutely dry conditions, in nitrogen atmosphere and away from light. 0.312 g of ethyl iodide are added (2 mM) and the solution is agitated for 15 hr at 30° C. 0.272 g of 1-8 dibromooctane are added (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

4.05 g of the compound featured in the title are obtained.

Ethoxyl determination is carried out according to the method of Cundiff et al. and shows a content of 2.05% w/w as ethanol (theoretical: 2.25). Total ester group analysis is carried out by saponification reaction of an excess quantity of NaOH 0.1N at 50° C. for 30 min. The excess is determined by titration with HCl 0.1N using phenolphthalein as an indicator. It is thus possible to determine a total ester group content of 0.96 mEq/g (theoretical: 0.98).

EXAMPLE 21

Preparation of hyaluronic acid (HY) partially esterified with ethanol and partially cross-linked with 1-8 octanediol 6.21 g of tetrabutylammonium salt of HY (10 mEq) are solubilized in 248 ml of DMSO at 25° C. in absolutely dry conditions, in nitrogen atmosphere and away from light. 0.624 g of ethyl iodide are added (4 mM) and the solution is agitated for 15 hr at 30° C. 0.272 g of 1-8 dibromooctane are added (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

3.99 g of the compound featured in the title are obtained.

Ethoxyl determination is carried out according to the method of Cundiff et al. and shows a content of 4.39% w/w as ethanol (theoretical: 4.49). Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 1.43 mEq/g (theoretical: 1.46).

EXAMPLE 22

Preparation of hyaluronic acid (HY) partially esterified with ethanol and partially cross-linked with 1-8 octanediol 6.21 g of tetrabutylammonium salt of HY (10 mEq) are solubilized in 248 ml of DMSO at 25° C. in absolutely dry conditions, in nitrogen atmosphere and away from light. 0.934 g of ethyl iodide are added (6 mM) and the solution is agitated for 15 hr at 30° C. 0.272 g of 1-8 dibromooctane are added (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

4.10 g of the compound featured in the title are obtained.

Ethoxyl determination is carried out according to the method of Cundiff et al. and shows a content of 6.66% w/w as ethanol (theoretical: 6.72). Total ester group analysis is carried out by saponification reaction with an excess quantity of of NaOH 0.1N at 50° C. for 30 min. The excess is determined by titration with HCl 0.1N using phenolphthalein as an indicator. It is thus possible to determine a total ester group content of 1.89 mEq/g (theoretical: 1.94).

EXAMPLE 23

Preparation of hyaluronic acid (HY) partially esterified with ethanol and partially cross-linked with 1-8 octanediol 6.21 g of tetrabutylammonium salt of HY (10 mEq) are solubilized in 248 ml of DMSO at 25° C. in absolutely dry conditions, in nitrogen atmosphere and away from light. 1.170 g of ethyl iodide are added (7.5 mM) and the solution is agitated for 15 hr at 30° C. 0.272 g of 1-8 dibromooctane are added (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

4.03 g of the compound featured in the title are obtained.

Ethoxyl determination is carried out according to the method of Cundiff et al. and shows a content of 8.27% w/w as ethanol (theoretical: 8.38). Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 2.05 mEq/g (theoretical: 2.3).

EXAMPLE 4

Preparation of hyaluronic acid (HY) partially esterified with ethanol and partially cross-linked with 1-8 octanediol 6.21 g of tetrabutylammonium salt of HY (10 mEq) are solubilized in 248 ml of DMSO at 25° C. in absolutely dry conditions, in nitrogen atmosphere and away from light. 0.624 g of ethyl iodide are added (4 mM) and the solution is agitated for 15 hr at 30° C. 0.544 g of 1-8 dibromooctane are added (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

4.15 g of the compound featured in the title are obtained.

Ethoxyl determination is carried out according to the method of Cundiff et al. and shows a content of 4.36% w/w as ethanol (theoretical: 4.42). Total ester group analysis is carried out by saponification reaction with an excess quantity of of NaOH 0.1N at 50° C. for 30 min. The excess is determined by titration with HCl 0.1N using phenolphthalein as an indicator. It is thus possible to determine a total ester group content of 1.90 mEq/g (theoretical: 1.92).

EXAMPLE 25

Preparation of hyaluronic acid (HY) partially esterified with ethanol and partially cross-linked with 1-10 decanediol 6.21 g of tetrabutylammonium salt of HY (10 mEq) are solubilized in 248 ml of DMSO at 25° C. in absolutely dry conditions, in nitrogen atmosphere and away from light. 0.312 g of ethyl iodide are added (2 mM) and the solution is agitated for 15 hr at 30° C. 0.300 g of 1-10 dibromodecane are added (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

4.12 g of the compound featured in the title are obtained.

Ethoxyl determination is carried out according to the method of Cundiff et al. and shows a content of 2.12% w/w as ethanol (theoretical: 2.24). Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 0.94 mEq/g (theoretical: 0.97).

EXAMPLE 26

Preparation of hyaluronic acid (HY) partially esterified with ethanol and partially cross-linked with 1-10 decanediol 6.21 g of tetrabutylammonium salt of HY (10 mEq) are solubilized in 248 ml of DMSO at 25° C. in absolutely dry conditions, in nitrogen atmosphere and away from light. 0.624 g of ethyl iodide are added (4 mM) and the solution is agitated for 15 hr at 30° C. 0.300 g of 1-10 dibromodecane are added (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

4.10 g of the compound featured in the title are obtained.

Ethoxyl determination is carried out according to the method of Cundiff et al. and shows a content of 4.36% w/w as ethanol (theoretical: 4.46). Total ester group analysis is carried out by saponification reaction with an excess quantity of of NaOH 0.1N at 50° C. for 30 min. The excess is determined by titration with HCl 0.1N using phenolphthalein as an indicator. It is thus possible to determine a total ester group content of 1.43 mEq/g (theoretical: 1.45).

EXAMPLE 27

Preparation of hyaluronic acid (HY) partially esterified with ethanol and partially cross-linked with 1-10 decanediol 6.21 g of tetrabutylammonium salt of HY (10 mEq) are solubilized in 248 ml of DMSO at 25° C. in absolutely dry conditions, in nitrogen atmosphere and away from light. 0.934 g of ethyl iodide are added (6 mM) and the solution is agitated for 15 hr at 30° C. 0.300 g of 1-10 dibromodecane (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

4.12 g of the compound featured in the title are obtained.

Ethoxyl determination is carried out according to the method of Cundiff et al. and shows a content of 6.5% w/w as ethanol (theoretical: 6.67). Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 1.87 mEq/g (theoretical: 1.93).

EXAMPLE 28

Preparation of hyaluronic acid (HY) partially esterified with ethanol and partially cross-linked with α,α'-paraxylene diol 6.21 g of tetrabutylammonium salt of HY (10 mEq) are solubilized in 248 ml of DMSO at 25° C. in absolutely dry conditions, in nitrogen atmosphere and away from light. 0.624 g of ethyl iodide are added (4 mM) and the solution is agitated for 15 hr at 30° C. 0.264 g of α,α'-dibromo-p-xylene are added (1 mM, corresponding to 2 mEq) and after homogenization the solution is kept at 30° for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

4.04 g of the compound featured in the title are obtained.

Ethoxyl determination is carried out according to the method of Cundiff et al. and shows a content of 4.4% p/p as ethanol (theoretical: 4.5). Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 1.36 mEq/g (theoretical: 1.47).

EXAMPLE 29

Preparation of hyaluronic acid (HY) partially esterified with benzyl alcohol and partially cross-linked with 1-8 octanediol 6.21 g of tetrabutylammonium salt of HY (10 mEq) are solubilized in 248 ml of DMSO at 25° C. in absolutely dry conditions, in nitrogen atmosphere and away from light. 0.342 g of benzyl bromide are added (2 mM) and the solution is agitated for 15 hr at 30° C. 0.272 g of dibromooctane are added (1 mM, corresponding to 2 mEq) and after homogenization the solution is kept at 30° C. for 24 hr.

For conversion of the residue tetrabutylammonium carboxy groups into sodium salt, to the resulting solution is added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

4.15 g of the compound featured in the title are obtained.

Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 0.93 mEq/g (theoretical: 0.95).

EXAMPLE 30

Preparation of hyaluronic acid (HY) partially esterified with benzyl alcohol and partially cross-linked with α,α'-paraxylenediol 6.21 g of tetrabutylammonium salt of HY (10 mEq) are solubilized in 248 ml of DMSO at 25° C. in absolutely dry conditions, in nitrogen atmosphere and away from light. 0.342 g of benzyl bromide are added (2 mM) and the solution is agitated for 15 hr at 30° C. 0.264 g of α,α'-dibromo-p-xylene (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

4.11 g of the compound featured in the title are obtained.

Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 0.92 mEq/g (theoretical: 0.95).

EXAMPLE 31

Preparation of hyaluronic acid (HY) partially cross-linked with 1-3 propanediol 6.21 g of tetrabutylammonium salt of HY (10 mEq) are solubilized in 248 ml of DMSO at 25° C. in absolutely dry conditions, in nitrogen atmosphere and away from light. 0.296 g of 1-3 diiodopropane are added (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

3.98 g of the compound featured in the title are obtained.

Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 0.47 mEq/g (theoretical: 0.499).

EXAMPLE 32

Preparation of hyaluronic acid (HY) partially cross-linked with 1-3 propanediol 6.21 g of tetrabutylammonium salt of HY (10 mEq) are solubilized in 248 ml of DMSO at 25° C. in absolutely dry conditions, in nitrogen atmosphere and away from light. 0.740 g of 1-3-diiodopropane are added (2.5 mM, corresponding to 5 mEq) and after homogenization the solution is kept at 30° C. for 24 hr.

For conversion of the residue tetrabutylammonium carboxy group s into sodium salt, to the resulting solution is added of 2.5 g of NaCl dissolved in 100 ml of distilled H₂O, while it is cooled from the outside with a bath of H₂O/ice.

500 ml of acetone are added, the precipitate is separated by filtration, washed 3 times with 100 ml of acetone/H₂O 5:1 and 3 times with 100 ml of pure acetone, and then vacuum dried.

3.89 g of the compound featured in the title are obtained.

Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 1.21 mEq/g (theoretical: 1.25).

EXAMPLE 33

Preparation of hyaluronic acid (HY) partially cross-linked with 1-3 propanediol 6.21 g of tetrabutylammonium salt of HY (10 mEq) are solubilized in 248 ml of DMSO at 25° C. with in rigourously damp-free conditions, in nitrogen atmosphere and away from light. 1.184 g of 1-3 diiodopropane are added (4 mM, corresponding to 8 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled H₂O, while it is cooled from the outside with a bath of H₂O/ice.

500 ml of acetone are added, the precipitate is separated by filtration, washed 3 times with 100 ml of acetone/H₂O 5:1 and 3 times with 100 ml of pure acetone, and then vacuum dried.

3.87 g of the compound featured in the title are obtained.

Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 1.97 mEq/g (theoretical: 2.00).

EXAMPLE 34

Preparation of hyaluronic acid (HY) partially cross-linked with 1-4 butanediol 6.21 g of tetrabutylammonium salt of HY (10 mEq) are solubilized in 248 ml of DMSO at 25° C. in absolutely dry conditions, in nitrogen atmosphere and away from light. 0.310 g of 1-4 diiodobutane are added (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled H₂O, while it is cooled from the outside with a bath of H₂O/ice.

500 ml of acetone are added, the precipitate is separated by filtration, washed 3 times with 100 ml of acetone/H₂O 5:1 and 3 times with 100 ml of pure acetone, and then vacuum dried.

4.00 g of the compound featured in the title are obtained.

Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 0.492 mEq/g (theoretical: 0.497).

EXAMPLE 35

Preparation of hyaluronic acid (HY) partially cross-linked with 1-6 hexanediol 6.21 g of tetrabutylammonium salt of HY (10 mEq) are solubilized in 248 ml of DMSO at 25° C. in absolutely dry conditions, in nitrogen atmosphere and away from light. 0.370 g of tetrabutylammonium iodide are added (1 mM) and the solution is agitated for 1 hr at 20° C. 0.244 g of 1-6 dibromohexane (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled H₂O, while cooling it from the outside with a bath of H₂O/ice.

500 ml of acetone are added, the precipitate is separated by filtration, washed 3 times with 100 ml of acetone/H₂O 5:1 and 3 times with 100 ml of pure acetone, and then vacuum dried.

4.01 g of the compound featured in the title are obtained.

Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 0.486 mEq/g (theoretical: 0.494).

EXAMPLE 36

Preparation of hyaluronic acid (HY) partially cross-linked with 1-8 octanediol 6.21 g of tetrabutylammonium salt of HY (10 mEq) are solubilized in 248 ml of DMSO at 25° C. in absolutely dry conditions, in nitrogen atmosphere and away from light. 0.370 g of tetrabutylammonium iodide (1 mM) and the solution is agitated for 1 hr at 20° C. 0.272 g of 1-8 dibromooctane are added (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled H₂O, while it is cooled from the outside with a bath of H₂O/ice.

500 ml of acetone are added, the precipitate is separated by filtration, washed 3 times with 100 ml of acetone/H₂O 5:1 and 3 times with 100 ml of pure acetone, and then vacuum dried.

4.02 g of the compound featured in the title are obtained.

Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 0.478 mEq/g (theoretical: 0.490).

EXAMPLE 37

Preparation of hyaluronic acid (HY) partially cross-linked with 1-10 decanediol 6.21 g of tetrabutylammonium salt of HY (10 mEq) are solubilized in 248 ml of DMSO at 25° C. in absolutely dry conditions, in nitrogen atmosphere and away from light. 0.369 g of iodide are added (1 mM) and the solution is agitated for 1 hr at 20° C. 0.300 g of 1-10 dibromodecane are added (1 mM, corresponding to 2 mEq) and after homogenization the solution is kept at 30° C. for 24 hr.

For conversion of the residue tetrabutylammonium carboxy groups into sodium salt, to the resulting solution are added 2.5 g of NaCl dissolved in 100 ml of distilled $H_2O$, while it is cooled from the outside with a bath of $H_2O$/ice.

500 ml of acetone are added, the precipitate is separated by filtration, washed 3 times with 100 ml of acetone/$H_2O$ 5:1 and 3 times with 100 ml of pure acetone, and then vacuum dried.

3.99 g of the compound featured in the title are obtained.

Total ester group analysis is carried out by saponification reaction with an excess quantity of NaOH 0.1N at 50° C. for 30 min. The excess is determined by titration with HCl 0.1N using phenolphthalein as an indicator. It is thus possible to determine a total ester group content of 0.476 mEq/g (theoretical: 0.487).

EXAMPLE 37A

Preparation of the (partial and mixed) octandiol and cortisone ester of hyaluronic acid (HY) - 40% of carboxylic groups esterified with octandiol - 20% of carboxylic groups esterified with cortisone ($C_{21}$) - 40% of carboxylic groups salified (Na).

6.2 g of HY tetrabutylammonium salt with a molecular weight of 125,000 corresponding to 10 m.Eq. of a monomeric unit are solubilized in 310 ml of dimethylsulfoxide at 25°, 1.09 g (4 m.Eq.) of 1,8-dibromooctane are added and the solution is kept for 24 hours at 30°. 0.85 q (2 m.Eq.) of 21-bromo-4-pregnene-17α-1-3, 11, 20-trione are added and the solution is kept for 24 hours at 30°.

A solution is then added containing 100 ml of water and 5 g of sodium chloride and the resulting mixture is slowly poured into 2,000 ml of acetone under constant agitation. A precipitate is formed which is filtered and washed three times with 100 ml of acetone/water 5:1 and three times with 100 ml of acetone and finally vacuum dried for eight hours at 30° C.

4.5 g of the compound featured in the title are obtained.

Quantitative determination of cortisone, after mild alkaline hydrolysis with hydroalcoholic solution of $Na_2CO_3$ and extraction with chloroform, is carried out according to British Pharmacopea, 1980, p. 224.

TABLE 1

| | PERCENTAGE COMPOSITION OF THE VARIOUS CROSS-LINKED PRODUCTS | | |
|---|---|---|---|
| EXAMPLES No. | No. OF ESTERIFIED CARBOXYLS PER 100 WITH ... | No. OF CROSS-LINKED CARBOXYLS PER 100 WITH ... | No. CARBOXYLS SALIFIED WITH SODIUM PER 100 |
| 1 | 5/$CH_3$—$CH_2$— | 5/—$(CH_2)_3$— | 90 |
| 2 | 5/$CH_3$—$CH_2$— | 10/—$(CH_2)_3$— | 85 |
| 3 | 5/$CH_3$—$CH_2$— | 20/—$(CH_2)_3$— | 75 |
| 4 | 10/$CH_3$—$CH_2$— | 20/—$(CH_2)_3$— | 70 |
| 5 | 20/$CH_3$—$CH_2$— | 20/—$(CH_2)_3$— | 60 |
| 6 | 40/$CH_3$—$CH_2$— | 20/—$(CH_2)_3$— | 40 |
| 7 | 60/$CH_3$—$CH_2$— | 20/—$(CH_2)_3$— | 20 |
| 8 | 75/$CH_3$—$CH_2$— | 20/—$(CH_2)_3$— | 5 |
| 9 | 40/$CH_3$—$CH_2$— | 40/—$(CH_2)_3$— | 20 |
| 10 | 20/$CH_3$—$CH_2$— | 20/—$(CH_2)_4$— | 60 |
| 11 | 40/$CH_3$—$CH_2$— | 20/—$(CH_2)_4$— | 40 |
| 12 | 60/$CH_3$—$CH_2$— | 20/—$(CH_2)_4$— | 20 |
| 13 | 20/$CH_3$—$CH_2$— | 20/—$(CH_2)_6$— | 60 |
| 14 | 40/$CH_3$—$CH_2$— | 20/—$(CH_2)_6$— | 40 |
| 15 | 60/$CH_3$—$CH_2$— | 20/—$(CH_2)_6$— | 20 |
| 16 | 5/$CH_3$—$CH_2$— | 5/—$(CH_2)_8$— | 90 |
| 17 | 5/$CH_3$—$CH_2$— | 10/—$(CH_2)_8$— | 85 |
| 18 | 5/$CH_3$—$CH_2$— | 20/—$(CH_2)_8$— | 75 |
| 19 | 10/$CH_3$—$CH_2$— | 20/—$(CH_2)_8$— | 70 |
| 20 | 20/$CH_3$—$CH_2$— | 20/—$(CH_2)_8$— | 60 |
| 21 | 40/$CH_3$—$CH_2$— | 20/—$(CH_2)_8$— | 40 |
| 22 | 60/$CH_3$—$CH_2$— | 20/—$(CH_2)_8$— | 20 |
| 23 | 75/$CH_3$—$CH_2$— | 20/—$(CH_2)_8$— | 5 |
| 24 | 40/$CH_3$—$CH_2$— | 40/—$(CH_2)_8$— | 20 |
| 25 | 20/$CH_3$—$CH_2$— | 20/—$(CH_2)_{10}$— | 60 |
| 26 | 40/$CH_3$—$CH_2$— | 20/—$(CH_2)_{10}$— | 40 |
| 27 | 60/$CH_3$—$CH_2$— | 20/—$(CH_2)_{10}$— | 20 |
| 28 | 40/$CH_3$—$CH_2$— | 20/—$(CH_2$—O—$CH_2)$— | 40 |
| 29 | 20/O—$CH_2$— | 20/—$(CH_2)_8$— | 60 |
| 30 | 20/O—$CH_2$— | 20/—$(CH_2$—O—$CH_2)$— | 60 |
| 31 | — | 20/—$(CH_2)_3$— | 80 |
| 32 | — | 50/—$(CH_2)_3$— | 50 |
| 33 | — | 80/—$(CH_2)_3$— | 20 |
| 34 | — | 20/—$(CH_2)_4$— | 80 |
| 35 | — | 20/—$(CH_2)_6$— | 80 |
| 36 | — | 20/—$(CH_2)_8$— | 80 |
| 37 | — | 20/—$(CH_2)_{10}$— | 80 |

EXAMPLE 38

Method by which a mixture of Hyalastine and Hyalectin fractions, with no inflammatory activity, may be obtained Fresh or frozen cocks' combs, (3000 g) are minced in a mincer and then carefully homogenized in a mechanical homogenizer. The paste thus obtained is placed in a AISI 316 stainless steel container or in glass and treated with 10 volumes of anhydrous acetone. The whole is agitated for 6 hours at a speed of 50 rpm. It is left to separate for 12 hrs and then the acetone is discarded by siphoning. Acetone extraction is repeated until the discarded acetone reaches the right degree of humidity (Karl-Fischer method). The whole is then centrifuged and vacuum dried at a suitable temperature for 5-8 hours. Approximately 500-600 gr of dry powdered cocks' combs are thus obtained.

300 gr. of dry powder are exposed to enzymatic digestion with papain (0.2 g) in aqueous medium buffered with phosphate buffer in the presence of a suitable quantity of hydrochloride cysteine. It is agitated for 24 hrs at 60 rpm at a constant temperature of 60°-65° C. The whole is then cooled to 25° C. and Celite ®(60 gr) is added, maintaining agitation for another hour. The mixture obtained is filtered until a clear liquid is obtained. The clear liquid is exposed to molecular ultrafiltration on membranes with a molecular exclusion limit of 30,000 to retain on the membrane those molecules with a molecular weight of over 30,000.

5 to 6 original volumes are ultrafiltered, continuously adding distilled water to the product being ultrafiltered. The addition of water is suspended and ultrafiltration is continued until the volume is reduced to ⅓ of the original. The residue liquid is brought to 0.1M with the addition of sodium chloride and the temperature is brought to 50° C. Under agitation of 60 rpm, 45 g of cetylpiridinium chloride are added. It is agitated for 60 minutes and then 50 g of Celite ® are added. Under agitation, the temperature of the whole is brought to 25° C. and the precipitate formed by centrifugation is gathered. The precipitate obtained is suspended in a 0.01M solution in sodium chloride (5 liters) containing 0.5% cetylpyridinium chloride. It is agitated for 60 minutes at 50° C.; the temperature is then brought to 25° C. and the precipitate is centrifuged. Washing is repeated 3 times and finally the precipitate is gathered in a recipient containing 3 liters of a 0.05M solution of sodium chloride containing 0.5% cetylpyridinium chloride.

It is agitated at 60 rpm for 60 minutes and the temperature is kept constant at 25° C. for two hours. The supernatant is eliminated by centrifugation. The procedure is repeated several times with solutions of 0.1M sodium chloride containing 0.05% of cetylpyridinium chloride. The mixture is centrifuged and the supernatant is discarded. The precipitate is dispersed in a solution of 0.30M sodium chloride containing 0.5% cetylpyridinium chloride (3 liters). The mixture is agitated and both the precipitate and the clear liquid are gathered. Extraction is repeated on the precipitate 3 more times, each time using 0.5 lt of the same aqueous solution.

Finally, the residue precipitate is eliminated and the clear liquids are gathered in a single container. The temperature of the liquid is brought to 50° C. while maintaining agitation. The liquid is then brought to 0.23M with sodium chloride. 1 gr of cetylpyridinium chloride is added, and agitation is maintained for 12 hrs.

The mixture is cooled to 25° C. and then filtered first on Celite ® and then through a filtre. It is then again exposed to molecular ultrafiltration on membrane with a molecular exclusion limit of 30.000 ultrafiltering three initial volumes with the addition of a 0.33M sodium chloride solution. The addition of sodium chloride solution is suspended and the volume is reduced to ¼ of the initial volume. The solution thus concentrated is precipitated under agitation (60 rpm) at 25° C. with 3 volumes of ethanol (95%). The precipitate is gathered by centrifugation and the supernatant is discarded. The precipitate is dissolved in 1 of 0.1M solution in sodium chloride and precipitation is repeated with 3 volumes of 95% ethanol. The precipitate is gathered and washed first with 75% ethanol 3 times, then with absolute ethanol (3 times), and lastly with absolute acetone (3 times).

The product thus obtained (HYALASTINE+HYALECTIN fractions) has an average molecular weight of between 250,000 and 350,000.

The yield of HY is equal to 0.6% of original fresh tissue.

EXAMPLE 39

Method for obtaining the fraction Hyalastine from the mixture obtained by the method described in Example 38.

The mixture obtained by the method described in Example 38 is dissolved in apyrogenic distilled water in a measure of 10 mg of product per 1 ml of water. The solution obtained is exposed to molecular filtration through filtre membranes with a molecular exclusion limit of 200,000, using a concentration technique without the addition of water on top of the membrane. During the ultrafiltration process through membranes with a molecular exclusion limit of 200,000, the molecules with a molecular weight of over 200,000 cannot pass, while the smaller molecules pass through the membrane together with the water. During the filtration procedure no water is added on top of the membrane; so that the volume diminishes, and consequently the concentration of molecules with a molecular weight of over 200,000 increases. Ultrafiltration is continued until the volume on top of the membrane is reduced to 10% of the initial volume. Two volumes of apyrogenic distilled water are added and it is again ultrafiltered until the volume is reduced to ⅓ of the original. The operation is repeated twice more. The solution passed through the membrane is brought to 0.1M with sodium chloride and is then precipitated with 4 volumes of 95% ethanol. The precipitate is washed 3 times with 75% ethanol and then vacuum dried.

The product thus obtained (HYALASTINE fraction) has an average molecular weight of between 50,000 and 100,000.

The yield of HY is equal to 0.4% of the original starting fresh tissue.

EXAMPLE 40

Method for obtaining the Hyalectin fraction

The concentrated solution gathered in the container on top of the ultrafiltration membrane with a molecular exclusion limit of 200,000 as in Example 39, is diluted with water until a solution containing 5 mg/ml of hyaluronic acid is obtained, as determined by quantitative analysis based on the dosage of glucuronic acid.

The solution is brought to 0.1M in sodium chloride and then precipitated with 4 volumes of 95% ethanol.

The precipitate is washed 3 times with 75% ethanol and then vacuum dried.

The product thus obtained (HYALECTIN fraction) has a molecular weight of between 500,000 and 730,000. This corresponds to a specific hyaluronic acid fraction with a molcular chain measuring between about 2,500 and 3,500 saccharide units and with a high degree of purity. The yield of HY is equal to 0.2% of original fresh starting tissue.

EXAMPLE 41

Preparation of films of cross-linked derivatives of hyaluronic acid (HY) and partially esterified with various alcohols The DMSO solutions, after addition of all the ingredients and after homogenization obtained as in Examples 6–15, 19–30 and 37, are layered in glass dishes to the desired thickness and in an atmosphere of nitrogen, in absolutely dry conditions and away from light for 24 hr. The films of cross-linked and esterified hyaluronic derivatives thus obtained and in which are also present tetrabutylammonium carboxy groups are dialyzed first in NaCl 1% and then in distilled $H_2O$ at 4° C., the solutions being changed periodically. The films containing sodium salts of the above cross-linked derivatives are then placed between two cellophane membranes and vacuum dried at 37° in a slab dryer.

MEDICAL PRODUCTS AND PHARMACEUTICAL PREPARATIONS

The pharmaceutical preparations containing the new cross-linked derivatives of the present invention and their salts as active principle, both in the case of cross-linked derivatives possibly further esterified and/or salified with therapeutically active alcohols and intended for the same indications as HY itself, and in the case of esters with therapeutically active alcohols intended for use in indications corresponding to such alcohols, contain the common excipients and may be destined for oral, rectal, parenteral, subcutaneous, local, intradermal or topical use. They are therefore in solid or semisolid form, for example, pills, tablets, gelatinous capsules, capsules, suppositories, soft gelatin capsules. For parenteral and subcutaneous uses, it is possible to use forms intended for intramuscular or intradermal administration, or suitable for infusion or intravenous injections. It is, therefore, possible to present active compounds as solutions or as freeze-dried powders active compounds to be pooled with one or more excipients or diluents which are pharmaceutically acceptable, and convenient for the above uses and with a type of osmolarity suitable for physiological liquids. For local use, preparations in spray form should be considered, for example nasal sprays, creams or ointments for topical use of plasters suitably prepared for intradermal administration.

The preparations of the invention may be destined for administration to man or animal. They contain Preferably between 0.01% and 10% of active component for solutions, sprays, ointments and creams and between 1% and 100% and preferably between 5% and 50% of the active compound for preparations in solid form. The dosage to be administered depends on the indication, on the desired effect and on the chosen administration route. The daily dosage of such preparations may be deduced from that in use for the corresponding known preparations both of hyaluronic acid for the corresponding cures, for example for the cure of arthritis, for example in man or in horse, and of therapeutically active alcohol the action of which is to be exploited. Thus, for example, the dosage of a hyaluronic ester with cortisone may be derived from its content in this ester and from its usual dosage in the known pharmaceutical preparations.

In cosmetic articles, the new cross-linked derivatives of the present invention and their salts are mixed with the excipients commonly used in this art and are for example those already listed above for pharmaceutical preparations. Above all, creams, ointments, lotions for topical use are used in which the new cross-linked derivatives of the present invention may constitute the active cosmetic principle possibly with the addition of other cosmetically active principles, such as steroids, for example pregnenolone, or one of the principles reported above. In these preparations, the new cross-linked derivatives of the present invention are preferably esters with an alcohol without any cosmetic action, such as a lower aliphatic alcohol, for example one of those already mentioned. In these preparations the effect is due to the intrinsic cosmetic properties of the polysaccharide component, as in the case of free hyaluronic acid or its salts.

The cosmetic articles may, however, be based on substances with specific actions which differ from those of hyaluronic acid, for example disinfectants, sun-shields, waterproofing or regenerating substances, or anti-wrinkle or odoriferous substances, especially perfumes. In this case the new cross-linked derivatives of the present invention may again be themselves the active ingredient and derive from alcohols with these properties, for example from higher aliphatic alcohols or terpene alcohols in the case of perfumes or may function above all as vehicles for substances with those properties with which they are associated. Particularly important, therefore, are cosmetic compositions similar to the medicaments described above in which the pharmaceutically active component is substituted by a cosmetological factor and the respective salts.

The use of the above esters deriving from the alcohols used in the perfume industry represents an important step forward in technique, since it allows for a slow, constant and prolonged release of the odorous principles.

One important application of the present invention regards the sanitary and surgical articles already described above, the methods for their manufacture and use. The invention therefore includes all the articles similar to those already on the market containing hyaluronic acid but also containing the new cross-linked derivatives of the present invention in place of the free acid or one of its salts, for example inserts or ophthalmic lenses.

Completely new surgical and sanitary articles according to the present invention are represented by the new cross-linked derivatives of the present invention regenerated as such by appropriate organic solutions capable of being made into sheet or thread form, thus obtaining films, sheets and threads for use in surgery, as auxiliaries and substitutes of the skin in cases of serious damage to this organ, for example following burns, or as suture threads in surgery. The invention includes in particular these uses and one preparation procedure of these articles consists in (a) forming a solution of a hyaluronic ester or one of its salts in a suitable organic solvent, for example a ketone, an ester or an aprotic solvent such as a carboxy acid amide, especially a dialkylamide of an aliphatic acid having between 1 and 5 carbon atoms and deriving from alkyl groups with between 1 and 6 carbon atoms, first and foremost from an organic sulfoxide, that is, a dialkylsulfoxide with alkyl groups with a maximum of 6 carbon atoms, such as especially dimethylsulfoxide or diethylsulfoxide and again first and foremost by a fluorinated solvent with a low boiling point such as especially hexafluoroisopropanol, (b) making this solution into sheet or thread form and (c) removing the organic solvent by contact with another organic or aqueous solvent which can be mixed with the first solvent and in which the hyaluronic ester is not soluble, especially a lower aliphatic alcohol, for example ethyl alcohol (Wet spinning), or if a solvent with a not too high boiling point has been used to prepare the solution of the hyaluronic derivative, in removing this solvent with a current of gas and especially suitably heated nitrogen (Dry spinning). It is also possible to use to great advantage the system of Dry-wet spinning.

The threads obtained with the new cross-linked derivatives of the present invention may be used for the preparation of lints for use in the medication of wounds and in surgery. The use of such lints has the exceptional advantage of their biodegradation in the organism, effected by the enzymes it contains. These enzymes split the ester in hyaluronic acid and in the corresponding alcohol and in a compound already present in the organism, or rather, an innocuous compound such as an alcohol. Such lints and also the above threads may also therefore be left inside the organism after surgery, since these are subsequently slowly absorbed due to the above degradation process.

In the preparation of the sanitary and surgical articles mentioned above, it is convenient to add plasicizing materials to enhance their mechanical characteristics, such as in case of threads, to improve their resistance to tangling. These plasticizers may be for example alkaline salts of fatty acids, for example sodium stearate or sodium palmitate, the esters of organic acids with many carbon atoms, etc.

Another application of the new cross-linked derivatives of the present invention where their biodegradable qualities are utilized by the esterases present in the organism, is represented by the preparation of capsules for subcutaneous implatation of medicaments or of microcapsules for injection, for example by subcutaneous and intramuscular route. For the application of subcutaneous medicaments for slow release and consequently a "retard" action, capsules made of silicon material have been used until today, with the disadvantage that such capsules are liable to migrate within the organism and it is impossible to recover them. Obviously, with the new cross-linked derivatives of the present invention this danger no longer exists. Of great importance also is the preparation of microcapsules containing the new cross-linked derivatives of the present invention, avoiding the problems usually connected with their use, until now quite limited for the reasons mentioned above. This preparation opens up a whole new area of applications where a "retard" effect by injection is to be obtained.

A further application of the new cross-linked derivatives of the present invention in the field of medicine and surgery is represented by the preparation of various solid inserts such such as plates, discs, sheets, etc. substituting the metallic ones those containing synthetic plastic material currently in use, in cases involving inserts intended for removal after a certain length of time. Preparations containing animal collagen, being of a proteic nature, often provoke unpleasant reactions, such as inflammation or rejection. In the case of the new cross-linked derivatives of the present invention, even though they originate from animal and not human hyaluronic acid, this danger does not exist, since there is no incompatibility between the polysaccharides of various animal species.

Another use is for the correction of defects and the augmentation of soft tissues. A need has been felt for some time for safe and efficient biomaterials with which to substitute soft tissues which have been removed or damaged. Many alloplasty materials including paraffin, teflon paste, silicon and bovine collagene have been used to substitute for lost soft tissue. However, these materials were associated with undesirable and permanent changes in the skin tissues, with migration in situ and with negative reactions. The need persists therefore for a versatile biomaterial for use in medicine. The new cross-linked derivatives of the present invention may be safely and effectively used to correct such defects of the soft tissues such as acne pimples, postsurgical atrophic irregularities, Mohs' chemosurgery, lacerated lip wounds and wrinkles caused by age.

Also included in the applications in the field of medicine and surgery of the new cross-linked derivatives of the present invention, are preparations made of expansive material, especially in the form of sponges, for the medication of wounds or lesions of various nature.

The following are typical examples of formulations prepared according to the invention.

| Formulation 1 - Collirium containing cortisone of which 100 ml contain: | |
|---|---|
| partial and mixed ester of hyaluronic acid with cortisone and octandiol (Ex. 37A) | gr. 0.300 |
| ethyl p. hydroxybenzoate | gr. 0.010 |
| methyl p. hydroxybenzoate | gr. 0.050 |
| sodium chloride | gr. 0.900 |
| water for injectable preparation/q.b.a. | ml. 100 |

| Formulation 2 - Cream containing a partial ester of hyaluronic acid with 1,3-propandiol, of which 100 gr. contain: | |
|---|---|
| partial ester of hyaluronic acid with 1,3-propandiol (Ex. 31) | gr. 0.2 |
| Polyethylenglycol monostearate 400 | gr. 10.000 |
| Cetiol V | gr. 5.000 |
| Lanette SX | gr. 2.000 |
| Paraoxybenzoate of methyl | gr. 0.075 |
| Paraoxybenzoate of propyl | gr. 0.050 |
| Sodium dihydroacetate | gr. 0.100 |
| Glycerine F.U. | gr. 1.500 |
| Sorbitol 70 | gr. 1.500 |
| Test cream | gr. 0.050 |
| Water for injectable preparation/q.b.a. | gr. 100.00 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. Total or partial cross-linked esters of hyaluronic acid with an aliphatic polyhydric alcohol, and salts of such partial esters with inorganic or organic bases, with the proviso that said cross-linked ester is not the cross-linked ester of hyaluronic acid with an alomethyloxirane or a bisepoxy compound 2. Cross-linked esters according to claim 1, wherein said aliphatic polyhydric alcohol is a dihydric alcohol.

3. Cross-linked esters according to claim 1, wherein said aliphatic polyhydric alcohol has between 2 and 16 carbon atoms.

4. Cross-linked esters according to claim 2, wherein said dihydric alcohol is a member selected from the group consisting of ethylene glycol, propylene glycol, butylene glycol, glycols derived from pentane, hexane, heptane and octane, and positional isomers thereof.

5. Cross-linked esters according to claim 1, wherein said aliphatic polyhydric alcohol is a member selected from the group consisting of glycerine, erythrite and pentaer/thrite.

6. Cross-linked esters according to claim 1, wherein at least one non-cross-linked carboxy group in said hyaluronic acid is esterified with an aliphatic alcohol having a maximum of 34 carbon atoms and wherein said aliphatic alcohol may be unsubstituted or substituted by one or two functional groups selected from the group consisting of amino, hydroxy, mercapto, aldehyde, keto, carboxy, hydrocarbyl and dihydrocarbylamino groups, ether, ester, thioether, thioester, acetal, ketal, carbalkoxy, carbamidic and substituted carbamidic groups substituted by one or two alkyl groups, the hydrocarbyl radicals in these functionally modified groups having a maximum of 6 carbon atoms, and in which such aliphatic alcohols may be interrupted in the carbon atom chain by heteroatoms selected from the group consisting of oxygen, sulphur and nitrogen.

7. Cross-linked esters according to claim 6, wherein said aliphatic alcohol is ethyl, propyl, isopropyl, n-butyl, isobutyl, tert-butyl alcohols, an amyl, pentyl, hexyl or octyl alcohol.

8. Cross-linked esters according to claim 1, wherein at least one non-cross-linked carboxy group in said hyaluronic acid is esterified with an araliphatic alcohol having only be benzene residue and in which the aliphatic chain has a maximum of 4 carbon atoms and in which the benzene residue may be substituted with between 1 and 3 methyl or hydroxy groups or with halogen atoms, and in which the aliphatic chain may be substituted with one or two functional groups selected from the group consisting of free- or mono- or diethyl amino groups, pyrrolidine and piperidine groups.

9. Cross-linked esters according to claim 1, wherein at least one non-cross-linked carboxy group in said hyaluronic acid is esterified with a cycloaliphatic alcohol or aliphatic-cycloaliphatic alcohol or heterocyclic alcohol which derives from a mono- or polycyclic carbohydrate with a maximum of 34 carbon atoms and is unsubstituted or substituted by one or more functional groups selected from the group consisting of amino, hydroxy, mercapto, aldehyde, keto, carboxy, hydrocarbyl- and dihydrocarbylamino groups, ether, ester, thioether, thioester, acetal, ketal, carbalkoxy, carbamidic and substituted carbamidic groups, by one or two alkyl groups, the hydrocarbyl radicals in these functionally modified groups having a maximum of 6 carbon atoms, and may be int errupted in the carbon atom chain by heteroatoms chosen from the group formed by oxygen, nitrogen and sulfur, and may have one or more aromatic bonds.

10. Cross-linked esters according to claim 9, wherein at least one of said non-cross-linked carboxy groups is esterified with an alcohol selected from the group consisting of cortisone, hydrocortisone, prednisone, prednisolone, fluorocortisone, dexamethasone, betamethasone, corticosterone, deoxysicorticosterone, paramethasone, flumethasone, flucinolone and its acetonide, fluprednylidene, clobetasol and beclomethasone.

11. Salts of partial esters according to claim 1, wherein said salt is a salt of said cross-linked ester with an alkaline or alkaline earth metal, magnesium or aluminum.

12. A sodium or ammonium salt of a cross-linked ester according to claim 11.

13. Salts of partial esters according to claim 1, wherein said salt is a salt of said partial cross-linked ester with ammonium, or with an aliphatic, araliphatic, cycloaliphatic or heterocyclic amine.

14. A pharmaceutical composition comprising an effective amount of a cross-linked ester according to claim 1 together with a pharmaceutically acceptable carrier, excipient or diluent.

15. A pharmaceutical composition comprising an effective amount of a cross-linked ester according to claim 1 as a vehicle, in admixture with a pharmacologically active agent.

16. A pharmaceutical composition comprising an effective amount of a cross-linked ester according to claim 8, wherein said alcohol esterified with said non-cross-linked carboxy group is a pharmacologically active alcohol.

17. A cosmetic article comprising as an active ingredient an effective amount of a cross-linked ester or a salt thereof according to claim 1.

18. A cosmetic article comprising as a cosmetic vehicle a cross-linked ester or a salt thereof according to claim 1.

19. A sanitary, medical or surgical article comprising a cross-linked ester or a salt thereof according to claim 1.

20. A sanitary, medical or surgical article according to claim 19, comprising a film of a cross-linked ester wherein said aliphatic polyhydric alcohol is a therapeutically inert alcohol.

21. A sanitary, medical or surgical article according to claim 19 comprising threads of a cross-linked ester wherein said aliphatic polyhydric alcohol is a therapeutically inert alcohol.

22. A capsule or microcapsule for medicaments comprising a cross-linked ester or a salt thereof according to claim 1.

23. A cross-linked ester of hyaluronic acid according to claim 1, wherein said ester is a total cross-linked ester.

24. A cross-linked ester of hyaluronic acid according to claim 2, wherein said ester is a total cross-linked ester.

25. A cross-linked ester of hyaluronic acid according to claim 4, wherein said ester is a total cross-linked ester.

26. A pharmaceutical composition comprising an effective amount of a cross-linked ester according to claim 2, together with a pharmaceutically acceptable carrier, excipient or diluent.

27. A pharmaceutical composition comprising an effective amount of a cross-linked ester according to 28. A pharmaceutical composition comprising an effective amount of a cross-linked ester according to claim 4, together with a pharmaceutically acceptable carrier, excipient or diluent.

29. A pharmaceutical composition comprising an effective amount of a cross-linked ester according to claim 5, together with a pharmaceutically acceptable carrier, excipient or diluent.

30. A pharmaceutical composition comprising an effective amount of a cross-linked ester according to claim 6, together with a pharmaceutically acceptable carrier, excipient or diluent.

31. A pharmaceutical composition comprising an effective amount of a cross-linked ester according to claim 7, together with a pharmaceutically acceptable carrier, excipient or diluent.

32. A pharmaceutical composition comprising an effective amount of a cross-linked ester according to claim 8, together with a pharmaceutically acceptable carrier, excipient or diluent.

33. A pharmaceutical composition comprising an effective amount of a cross-linked ester according to claim 9, together with a pharmaceutically acceptable carrier, excipient or diluent.

34. A pharmaceutical composition comprising an effective amount of a cross-linked ester according to claim 10, together with a pharmaceutically acceptable carrier, excipient or diluent.

35. A pharmaceutical composition comprising an effective amount of a cross-linked ester according to claim 11, together with a pharmaceutically acceptable carrier, excipient or diluent.

36. A pharmaceutical composition comprising an effective amount of a cross-linked ester according to claim 12, together with a pharmaceutically acceptable carrier, excipient or diluent.

37. A pharmaceutical composition comprising an effective amount of a cross-linked ester according to claim 13, together with a pharmaceutically acceptable carrier, excipient or diluent.

38. A pharmaceutical composition comprising an effective amount of a cross-linked ester according to claim 23, together with a pharmaceutically acceptable carrier, excipient or diluent.

39. A pharmaceutical composition comprising an effective amount of a cross-linked ester according to claim 24, together with a pharmaceutically acceptable carrier, excipient or diluent.

40. A pharmaceutical composition comprising an effective amount of a cross-linked ester according to claim 25, together with a pharmaceutically acceptable carrier, excipient or diluent.

40. A pharmaceutical composition which comprises from 10 to 90% of a cross-linked ester according to claim 1, together with a pharmaceutically acceptable carrier, excipient, or diluent.

41. A pharmaceutical composition which comprises from 10 to 90% of a cross-linked ester according to claim 2, together with a pharmaceutically acceptable carrier, excipient, or diluent.

42. A pharmaceutical composition which comprises from 10 to 90% of a cross-linked ester according to claim 4, together with a pharmaceutically acceptable carrier, excipient, or diluent.

43. A pharmaceutical composition which comprises from 10 to 90% of a cross-linked ester according to claim 5, together with a pharmaceutically acceptable carrier, excipient, or diluent.

44. A pharmaceutical composition which comprises from 10 to 90% of a cross-linked ester according to claim 6, together with a pharmaceutically acceptable carrier, excipient, or diluent.

45. A pharmaceutical composition which comprises from 10 to 90% of a cross-linked ester according to claim 7, together with a pharmaceutically acceptable carrier, excipient, or diluent.

46. A pharmaceutical composition which comprises from 10 to 90% of a cross-linked ester according to claim 8, together with a pharmaceutically acceptable carrier, excipient, or diluent.

47. A pharmaceutical composition which comprises from 10 to 90% of a cross-linked ester according to claim 9, together with a pharmaceutically acceptable carrier, excipient, or diluent.

48. A pharmaceutical composition which comprises from 10 to 90% of a cross-linked ester according to claim 10, together with a pharmaceutically acceptable carrier, excipient, or diluent.

49. A pharmaceutical composition which comprises from 10 to 90% of a cross-linked ester according to claim 11, together with a pharmaceutically acceptable carrier, excipient, or diluent.

50. A pharmaceutical composition which comprises from 10 to 90% of a cross-linked ester according to claim 12, together with a pharmaceutically acceptable carrier, excipient, or diluent.

51. A pharmaceutical composition which comprises from 10 to 90% of a cross-linked ester according to claim 13, together with a pharmaceutically acceptable carrier, excipient, or diluent.

52. A pharmaceutical composition which comprises from 10 to 90% of a cross-linked ester according to claim 23, together with a pharmaceutically acceptable carrier, excipient, or diluent.

53. A pharmaceutical composition which comprises from 10 to 90% of a cross-linked ester according to claim 24, together with a pharmaceutically acceptable carrier, excipient, or diluent.

54. A pharmaceutical composition which comprises from 10 to 90% of a cross-linked ester according to claim 25, together with a pharmaceutically acceptable carrier, excipient, or diluent.

55. A pharmaceutical composition which comprises from 10 to 90% of a cross-linked ester according to claim 1 as a vehicle, in admixture with a pharmacologically active agent.

56. A pharmaceutical composition which comprises from 10 to 90% of a cross-linked ester according to any one of claim 2, 4–10, 11–13 and 23, 25, in admixture with a pharmacologically active agent.

57. A pharmaceutical composition which comprises from 10–90% by weight of a cross-linked ester according to claim 8, wherein said alcohol esterified with said non-cross-linked carboxy group is a pharmacologically active alcohol.

58. A cosmetic article which comprises as an active ingredient from 5–50% by weight of a cross-linked ester or a salt thereof according to claim 1.

59. A cosmetic article which comprises as an active ingredient from 5–50% by weight of a cross-linked ester or a salt thereof according to claim 2.

60. A cosmetic article which comprises as an active ingredient from 5–50% by weight of a cross-linked ester or a salt thereof according to claim 4.

61. A cosmetic article which comprises as an active ingredient from 5–50% by weight of a cross-linked ester or a salt thereof according to claim 5.

62. A cosmetic article which comprises as an active ingredient from 5-50% by weight of a cross-linked ester or a salt thereof according to claim 7.

63. A cosmetic article which comprises as an active ingredient from 5-50% by weight of a cross-linked ester or a salt thereof according to claim 10.

64. A cosmetic article which comprises as an active ingredient from 5-50% by weight of a cross-linked ester or a salt thereof according to claim 23.

65. A cosmetic article which comprises as an active ingredient from 5-50% by weight of a cross-linked ester or a salt thereof according to claim 24.

66. A cosmetic article which comprises as an active ingredient from 5-50% by weight of a cross-linked ester or a salt thereof according to claim 25.

67. A cosmetic article comprising as a cosmetic vehicle a cross-linked ester or a salt thereof according to claim 2.

68. A cosmetic article comprising as a cosmetic vehicle a cross-linked ester or a salt thereof according to claim 4.

69. A cosmetic article comprising as a cosmetic vehicle a cross-linked ester or a salt thereof according to claim 23.

70. A cosmetic article comprising as a cosmetic vehicle a cross-linked ester or a salt thereof according to claim 24.

71. A sanitary, medical or surgical article comprising a cross-linked ester or a salt thereof according to claim 2.

72. A sanitary, medical or surgical article comprising a cross-linked ester or a salt thereof according to claim 4.

73. A sanitary, medical or surgical article comprising a cross-linked ester or a salt thereof according to claim 23.

74. A sanitary, medical or surgical article comprising a cross-linked ester or a salt thereof according to claim 24.

75. A sanitary, medical or surgical article according to claim 2, comprising a film of a cross-linked ester wherein said aliphatic polyhydric alcohol is a therapeutically inert alcohol.

76. A sanitary, medical or surgical article according to claim 4, comprising a film of a cross-linked ester wherein said aliphatic polyhydric alcohol is a therapeutically inert alcohol.

77. A sanitary, medical or surgical article according to claim 23, comprising a film of a cross-linked ester wherein said aliphatic polyhydric alcohol is a therapeutically inert alcohol.

78. A sanitary, medical or surgical article according to claim 24, comprising a film of a cross-linked ester wherein said aliphatic polyhydric alcohol is a therapeutically inert alcohol.

79. A sanitary, medical or surgical article according to claim 2 comprising threads of a cross-linked ester wherein said aliphatic polyhydric alcohol is a therapeutically inert alcohol.

80. A sanitary, medical or surgical article according to claim 4 comprising threads of a cross-linked ester wherein said aliphatic polyhydric alcohol is a therapeutically inert alcohol.

81. A sanitary, medical or surgical article according to claim 23 comprising threads of a cross-linked ester wherein said aliphatic polyhydric alcohol is a therapeutically inert alcohol.

82. A sanitary, medical or surgical article according to claim 24 comprising threads of a cross-linked ester wherein said aliphatic polyhydric alcohol is a therapeutically inert alcohol.

83. A capsule or microcapsule for medicaments comprising a cross-linked ester or a salt thereof according to claim 2.

84. A capsule or microcapsule for medicaments comprising a cross-linked ester or a salt thereof according to claim 4.

85. A capsule or microcapsule for medicaments comprising a cross-linked ester or a salt thereof according to claim 7.

86. A capsule or microcapsule for medicaments comprising a cross-linked ester or a salt thereof according to claim 8.

87. A capsule or microcapsule for medicaments comprising a cross-linked ester or a salt thereof according to claim 9.

88. A capsule or microcapsule for medicaments comprising a cross-linked ester or a salt thereof according to claim 10.

89. A capsule or microcapsule for medicaments comprising a cross-linked ester or a salt thereof according to claim 23.

90. A capsule or microcapsule for medicaments comprising a cross-linked ester or a salt thereof according to claim 24.

91. A capsule or microcapsule for medicaments comprising a cross-linked ester or a salt thereof according to claim 25.

* * * * *